(12) United States Patent
Kostarelos et al.

(10) Patent No.: US 11,598,779 B2
(45) Date of Patent: Mar. 7, 2023

(54) DETECTION OF CANCER BIOMARKERS USING NANOPARTICLES

(71) Applicant: THE UNIVERSITY OF MANCHESTER, Manchester (GB)

(72) Inventors: Kostas Kostarelos, Manchester (GB); Marilena Hadjidemetriou, Nicosia (CY)

(73) Assignee: THE UNIVERSITY OF MANCHESTER, Manchester (GB)

( * ) Notice: Subject to any disclaimer, the term of this patent is extended or adjusted under 35 U.S.C. 154(b) by 467 days.

(21) Appl. No.: 16/330,358

(22) PCT Filed: Sep. 6, 2017

(86) PCT No.: PCT/EP2017/072349
§ 371 (c)(1),
(2) Date: Mar. 4, 2019

(87) PCT Pub. No.: WO2018/046542
PCT Pub. Date: Mar. 15, 2018

(65) Prior Publication Data
US 2021/0132071 A1    May 6, 2021

(30) Foreign Application Priority Data
Sep. 6, 2016 (GB) .................................... 1615128

(51) Int. Cl.
*G01N 33/574* (2006.01)
*G01N 33/543* (2006.01)
(52) U.S. Cl.
CPC ... *G01N 33/57488* (2013.01); *G01N 33/5432* (2013.01)

(58) Field of Classification Search
CPC ................. G01N 33/57488; G01N 33/5432
See application file for complete search history.

(56) References Cited

U.S. PATENT DOCUMENTS

2012/0046184 A1\* 2/2012 Dawson ............. G01N 33/6872
506/9
2012/0328594 A1\* 12/2012 McKenna ................ A61P 3/10
424/94.4

(Continued)

FOREIGN PATENT DOCUMENTS

| EP | 2957912 A1 | 12/2015 |
| WO | 2010097785 A1 | 9/2010 |
| WO | 2011088128 A2 | 7/2011 |

OTHER PUBLICATIONS

Colapicchioni, Valentina et al., "Personalized liposome-protein corona in the blood of breast, gastricand pancreatic cancer patients," Sep. 11, 2015, The International Journal of Biochemistry & Cell Biology, Iss. 75, pp. 180-187. (Year: 2015).\*

(Continued)

*Primary Examiner* — Jennifer Wecker
*Assistant Examiner* — Michael Paul Shimek
(74) *Attorney, Agent, or Firm* — Polsinelli PC

(57) ABSTRACT

Methods for identifying and detecting potential disease specific biomarkers from biofluids. The methods involve in vivo administration of nanoparticles to a subject in a diseased state or incubating nanoparticles in a biofluid sample taken from a subject in a diseased state and analysis of the biomolecule corona formed on said nanoparticles. The methods distinguish between a healthy and diseased state in a subject, such as, for example, the presence of a tumor in a human subject.

13 Claims, 22 Drawing Sheets

(56) References Cited

U.S. PATENT DOCUMENTS

| | | | |
|---|---|---|---|
| 2013/0052661 A1* | 2/2013 | Huo | G01N 33/54346 435/7.21 |
| 2013/0058923 A1 | 3/2013 | Huo | |
| 2014/0087401 A1* | 3/2014 | Vortmeyer | G01N 33/542 435/7.92 |

OTHER PUBLICATIONS

Hadjidemetriou, Marilena et al., "In Vivo Biomolecule Corona around Blood-Circulating, Clinically Used and Antibody-Targeted Lipid Bilayer Nanoscale Vesicles," Jul. 2, 2015, ACS Nano, vol. 9, No. 8, pp. 8142-8156. (Year: 2015).*

Arvizo, et al., "Identifying New Therapeutic Targets via Modulation of Protein Corona Formation by Engineered Nanoparticles," Mar. 19, 2012, PLoS ONE, vol. 7, Iss. 3, pp. 1-8, doi:10.1371/journal.pone.0033650. (Year: 2 012).*

Qun Huo, Jimmie Colon, et al., "A Facile Nanoparticle Immunoassay for Cancer Biomarker Discovery," May 23, 2011, Journal of Nanobiotech., vol. 9, Iss. 7, pp. 1-12, doi:10.1186/1477-3155-9-20. (Year: 2011).*

Zhang et al. "Evaluation of a novel, integrated approach using functionalized magnetic beads, bench-top MALDI-TOF-MS with prestructured sample supports, and pattern recognition software for profiling potential biomarkers in human plasma." Journal of Biomolecular Techniques: JBT 15.3 (2004): 167. (Year: 2004).*

Miotto Giovanni et al: "Protein corona as a proteome fingerprint: The example of hidden biomarkers for cow mastitis", Colloids and Surfaces. B, Biointerfaces, Elsevier, Amsterdam, NL, vol. 140, Dec. 19, 2015, pp. 40-49, XP029413078, ISSN: 0927-7765.

Colapicchioni Valentina et al: "Personalized liposome-protein corona in the blood of breast, gastric and pancreatic cancer patients", International Journal of Biochemistry and Cell Biology, Pergamon, GB, vol. 75, Sep. 11, 2015, pp. 180-187, XP029537283, ISSN: 1357-2725.

Mohammad Javad Hajipour et al: "Personalized disease-specific protein corona influences the therapeutic impact of graphene oxide", Nanoscale, vol. 7, No. 19, Jan. 1, 2015, pp. 8978-8994, XP055424912, United Kingdom ISSN: 2040-3364.

Marilena Hadjidemetriou et al: "In Vivo Biomolecule Corona around Blood-Circulating, Clinically Used and Antibody-Targeted Lipid Bilayer Nanoscale Vesicles", ACS Nano, vol. 9, No. 8, Aug. 25, 2015, pp. 8142-8156, XP055424931, ISSN: 1936-0851.

Stefan Schrittwi Eser et al: Direct protein quantification in complex sample solutions by surface-engineered nanorod probes11 , Scientific Reports, vol. 7, No. 1, Jul. 6, 2017, XP055424973, whole document.

Arafeh Bigdeli et al: "Exploring Cellular Interactions of Liposomes Using Protein Corona Fingerprints and Physicochemical Properties", ACS Nano, vol. 10, No. 3, Mar. 22, 2016, pp. 3723-3737, XP055424948, US ISSN: 1936-0851.

Sandra Ritz: "Protein Corona of Nanoparticles: Distinct Proteins Regulate the Cellular Uptake11 , Biomacromolecules," vol. 16, No. 4, Apr. 13, 2015, pp. 1311-1321, XP055424953, ISSN: 1525-7797.

Qun Huo, et al.: "Developing a Nanoparticle Test for Prostate Cancer Scoring", Journal of Translational Medicine 2012, 10:44, BioMed Central, pp. 1-8.

Tianyu Zheng, et al.: "Gold Nanoparticle-Enabled Blood Test for Early Stage Cancer Detection and Risk Assessment", Appled Materials Interfaces 2015, 7, ACS Publications, 2015 American Chemical Society, pp. 2619-6827.

International Search Report and Written Opinion for corresponding PCT application No. PCT/EP2017/072349, dated Nov. 30, 2017.

Qun Huo et al., "A Facile Nanoparticle Immunoassay for Cancer Biomarker Discovery," Journal of Nanobiotechnology, vol. 9, No. 20, 2011; pp. 1-12.

S. Plachetti et al., "Exploitation of nanoparticle-protein corona for emerging therapeutic and diagnostic applications," Journal of Materials Chemistry B, vol. 4, 2016; pp. 4376-4381.

Hans-Dieter Zucht et al., "Casocidin-I: a casein-αs2 derived peptide exhibits antibacterial activity," FEBS Letters, vol. 372, 1995; pp. 185-188.

Tanaka, M. et al., "Increased levels of IgG antibodies against peptides of the prostate stem cell antigen in the plasma of pancreatic cancer patients," Oncology Report, No. 18, 2007, pp. 161-166.

* cited by examiner

| Max fold change | Highest mean condition | Lowest mean condition | Description | Accession |
|---|---|---|---|---|
| 489.35 | Healthy | Tumour | Protein Igkv15-103 | tr\|A0A087WNI5\|A0A087WNI5_MOUSE |
| 72.28 | Tumour | Healthy | Protein Ighv1-81 | tr\|A0A075B5Y4\|A0A075B5Y4_MOUSE;tr\|A0A075B5U8\|A0A075B5U8_MOUSE;tr\|X5J5S9\|X5J5S9_MOUSE |
| 56.76 | Tumour | Healthy | Ig kappa chain V-III region PC 7043 | sp\|P01665\|KV3AD_MOUSE;sp\|P01654\|KV3A1_MOUSE;sp\|P01664\|KV3AC_MOUSE;tr\|A0A087WNK6\|A0A087WNK6_MOUSE;tr\|A0A087WNK7\|A0A087WNK7_MOUSE |
| 46.47 | Tumour | Healthy | Protein Igkv2-109 | tr\|A0A075B5K6\|A0A075B5K6_MOUSE |
| 41.48 | Tumour | Healthy | Protein Ighv5-9-1 | tr\|A0A075B5Q6\|A0A075B5Q6_MOUSE;tr\|K7T935\|K7T935_MOUSE |
| 41.39 | Tumour | Healthy | Complement factor B (Fragment) | tr\|H3BK9S\|H3BK9S_MOUSE |
| 24.24 | Tumour | Healthy | Protein Igkv4-79 | tr\|A0A075B5L8\|A0A075B5L8_MOUSE |
| 21.88 | Tumour | Healthy | Ig kappa chain V-III region ABPC 22/PC 9245 | sp\|P01662\|KV3AA_MOUSE |
| 19.81 | Tumour | Healthy | Aldehyde dehydrogenase family 16 member A1 | tr\|D3Z089\|D3Z089_MOUSE;tr\|F6RQF0\|F6RQF0_MOUSE;tr\|Q9CWT9\|Q9CWT9_MOUSE |
| 18.33 | Healthy | Tumour | Ig gamma-2A chain C region secreted form | sp\|P01864\|GCAB_MOUSE |
| 13.19 | Healthy | Tumour | Protein Igha | tr\|A0A075B6A3\|A0A075B6A3_MOUSE |
| 12.99 | Tumour | Healthy | Pterin-mimicking anti-idiotope heavy chain variable region (Fragment) | tr\|Q920E7\|Q920E7_MOUSE |
| 10.68 | Tumour | Healthy | Ig mu chain C region | sp\|P01872\|IGHM_MOUSE |
| 10.68 | Tumour | Healthy | Ig mu chain C region | tr\|A0A075B5P6\|A0A075B5P6_MOUSE;tr\|A0A075B6A0\|A0A075B6A0_MOUSE |
| 10.42 | Tumour | Healthy | Tripeptidyl-peptidase 2 | sp\|Q64514\|TPP2_MOUSE;tr\|A0A087WQR6\|A0A087WQR6_MOUSE |
| 10.04 | Tumour | Healthy | IgG1 heavy chain VDJ region (Fragment) | tr\|X5J541\|X5J541_MOUSE |
| 9.38 | Tumour | Healthy | Signal transducer and activator of transcription | tr\|Q3TW11\|Q3TW11_MOUSE |
| 8.89 | Tumour | Healthy | Protein 4732456N10Rik | tr\|E9Q1Z0\|E9Q1Z0_MOUSE |
| 8.74 | Healthy | Tumour | IgM heavy chain VDJ region (Fragment) | tr\|X5J5N0\|X5J5N0_MOUSE;sp\|P01821\|HVM45_MOUSE |
| 8.33 | Tumour | Healthy | Ig heavy chain V region 23 | sp\|P01748\|HVM04_MOUSE |
| 8.24 | Tumour | Healthy | Betaine--homocysteine S-methyltransferase 1 | sp\|O35490\|BHMT1_MOUSE |
| 8.22 | Tumour | Healthy | Glycogen phosphorylase, brain form | sp\|Q8CI94\|PYGB_MOUSE |
| 7.12 | Tumour | Healthy | IgM heavy chain VDJ region (Fragment) | tr\|X5J5A3\|X5J5A3_MOUSE |
| 6.72 | Healthy | Tumour | Fibronectin | tr\|Q4KL80\|Q4KL80_MOUSE |
| 6.14 | Tumour | Healthy | Protein 4.1 | sp\|P48193\|41_MOUSE;tr\|F7BUB8\|F7BUB8_MOUSE |
| 5.92 | Tumour | Healthy | Fructose-bisphosphate aldolase | tr\|A6ZI46\|A6ZI46_MOUSE |
| 5.72 | Tumour | Healthy | Cytochrome P450, family 2, subfamily d, polypeptide 40 | tr\|Q5M8Q6\|Q5M8Q6_MOUSE |
| 5.71 | Tumour | Healthy | Proteoglycan 4 | tr\|E0CZ58\|E0CZ58_MOUSE |
| 5.65 | Healthy | Tumour | Carboxypeptidase | tr\|G3X8T3\|G3X8T3_MOUSE |
| 5.48 | Tumour | Healthy | B9-scFv | tr\|A2NN81\|A2NN81_MOUSE |
| 5.43 | Tumour | Healthy | H-2 class I histocompatibility antigen, alpha chain (Fragment) | sp\|P01895\|HA1Y_MOUSE |
| 5.42 | Healthy | Tumour | Putative uncharacterized protein | tr\|Q9DBN0\|Q9DBN0_MOUSE |
| 5.23 | Tumour | Healthy | Light chain variable region (Fragment) | tr\|A2NVX0\|A2NVX0_MOUSE |
| 5.16 | Tumour | Healthy | Liver carboxylesterase 1 | sp\|Q8VCC2\|EST1_MOUSE |

FIG. 4(a)

| Max fold change | Highest mean condition | Lowest mean condition | Description | Accession |
|---|---|---|---|---|
| 74.82 | Tumour | Healthy | Protein Igkv13-84 | tr\|A0A087WNI8\|A0A087WNI8_MOUSE |
| 55.62 | Healthy | Tumour | Putative uncharacterized protein | tr\|Q9D8L4\|Q9D8L4_MOUSE;sp\|P06327\|HVM52_MOUSE;tr\|A0A075B5T4\|A0A07585T4_MOUSE |
| 25.83 | Healthy | Tumour | Protein BC094916 | tr\|E9PVL3\|E9PVL3_MOUSE |
| 25.19 | Tumour | Healthy | Ig kappa chain V-VI region XRPC 44 | sp\|P01675\|KV6A1_MOUSE |
| 19.86 | Tumour | Healthy | Anti-H5N1 hemagglutinin monoclonal anitbody H5M9 heavy chain (Fragment) | tr\|U5LP42\|U5LP42_MOUSE |
| 19.46 | Tumour | Healthy | Putative uncharacterized protein | tr\|Q3UEW2\|Q3UEW2_MOUSE |
| 15.26 | Tumour | Healthy | Putative uncharacterized protein (Fragment) | tr\|Q3UH12\|Q3UH12_MOUSE |
| 13.93 | Tumour | Healthy | Filamin-A (Fragment) | tr\|F7AVL7\|F7AVL7_MOUSE |
| 11.70 | Tumour | Healthy | Calcium-activated chloride channel regulator 1 | sp\|Q9D7Z6\|CLCA1_MOUSE |
| 11.55 | Healthy | Tumour | Mucin 13, epithelial transmembrane, isoform CRA_a | tr\|Q3V1S6\|Q3V1S6_MOUSE |
| 10.31 | Healthy | Tumour | Immnuoglobulin kappa light chain (Fragment) | tr\|A2NVE9\|A2NVE9_MOUSE |
| 10.25 | Tumour | Healthy | Cytochrome b5 | tr\|E0CY88\|E0CY88_MOUSE |
| 9.51 | Tumour | Healthy | E2/E3 hybrid ubiquitin-protein ligase UBE2O | sp\|Q6ZPJ3\|UBE2O_MOUSE |
| 9.45 | Tumour | Healthy | Putative uncharacterized protein | tr\|Q3UGS0\|Q3UGS0_MOUSE |
| 9.00 | Healthy | Tumour | Fibronectin | tr\|Q4KL80\|Q4KL80_MOUSE |
| 8.76 | Tumour | Healthy | Putative uncharacterized protein | tr\|Q3UEM7\|Q3UEM7_MOUSE |
| 8.70 | Tumour | Healthy | Protein Ighv8-8 | tr\|A0A075B5W8\|A0A075B5W8_MOUSE |
| 8.65 | Healthy | Tumour | Leukemia inhibitory factor receptor | sp\|P42703\|LIFR_MOUSE |
| 8.56 | Healthy | Tumour | Pterin-mimicking anti-idiotope heavy chain variable region (Fragment) | tr\|Q920E7\|Q920E7_MOUSE |
| 8.43 | Healthy | Tumour | Fibrinogen, B beta polypeptide, isoform CRA_a | tr\|Q3TGR2\|Q3TGR2_MOUSE |
| 8.41 | Tumour | Healthy | alpha-1,2-Mannosidase | tr\|Q544T7\|Q544T7_MOUSE |
| 8.37 | Healthy | Tumour | Keratin, type II cytoskeletal 72 | sp\|Q6IME9\|K2C72_MOUSE |
| 8.25 | Tumour | Healthy | Sarcoplasmic/endoplasmic reticulum calcium ATPase 1 | sp\|Q8R429\|AT2A1_MOUSE |
| 8.17 | Healthy | Tumour | Putative uncharacterized protein | tr\|Q3V3W7\|Q3V3W7_MOUSE;tr\|Q3TQH1\|Q3TQH1_MOUSE |
| 8.02 | Healthy | Tumour | Oxidation resistance protein 1 | tr\|D3YXF5\|D3YXF5_MOUSE |
| 7.69 | Tumour | Healthy | Protein Ighv1-47 | tr\|A0A075B5V8\|A0A075B5V8_MOUSE |
| 7.68 | Healthy | Tumour | Gamma actin-like protein | tr\|Q9QZ83\|Q9QZ83_MOUSE |
| 7.63 | Healthy | Tumour | Fibrinogen alpha chain | sp\|E9PV24\|FIBA_MOUSE;tr\|Q08284\|Q08284_MOUSE |
| 7.49 | Tumour | Healthy | Ribosomal protein L15 | tr\|Q3U7D2\|Q3U7D2_MOUSE |
| 7.17 | Tumour | Healthy | 40S ribosomal protein S8 | tr\|Q5M9L9\|Q5M9L9_MOUSE;tr\|Q3UA25\|Q3UA25_MOUSE |
| 7.02 | Healthy | Tumour | Desmin | sp\|P31001\|DESM_MOUSE |
| 7.00 | Tumour | Healthy | Serum amyloid A protein | tr\|Q64454\|Q64454_MOUSE |
| 6.87 | Tumour | Healthy | Uncharacterized protein | tr\|F6YVP7\|F6YVP7_MOUSE |
| 6.72 | Healthy | Tumour | Protein Igkv4-79 | tr\|A0A075B5L8\|A0A075B5L8_MOUSE |
| 6.70 | Tumour | Healthy | UbiE1 | tr\|Q1XG79\|Q1XG79_MOUSE;tr\|H3BJI7\|H3BJI7_MOUSE |
| 6.25 | Healthy | Tumour | Putative uncharacterized protein | tr\|Q3U6I5\|Q3U6I5_MOUSE |
| 6.19 | Tumour | Healthy | Charged multivesicular body protein 4b | sp\|Q9D8B3\|CHM4B_MOUSE |
| 6.06 | Healthy | Tumour | Putative uncharacterized protein (Fragment) | tr\|Q3TRH4\|Q3TRH4_MOUSE |
| 6.03 | Tumour | Healthy | 60S ribosomal protein L36 | tr\|Q5M9L1\|Q5M9L1_MOUSE |
| 5.92 | Tumour | Healthy | Microsomal glutathione S-transferase 1 | tr\|D3YU60\|D3YU60_MOUSE |
| 5.90 | Healthy | Tumour | C4a protein | tr\|B9EIU2\|B9EIU2_MOUSE |
| 5.61 | Tumour | Healthy | 3-keto-steroid reductase | tr\|Q8C5N9\|Q8C5N9_MOUSE |
| 5.56 | Tumour | Healthy | Myosin-9 | sp\|Q8VDD5\|MYH9_MOUSE;tr\|A2VCK0\|A2VCK0_MOUSE;tr\|Q14B05\|Q14B05_MOUSE;tr\|Q3UFT0\|Q3UFT0_MOUSE;tr\|Q7TQJ6\|Q7TQJ6_MOUSE;tr\|Q811J9\|Q811J9_MOUSE |
| 5.43 | Tumour | Healthy | Alpha-1 type I procollagen (Fragment) | tr\|Q60785\|Q60785_MOUSE |
| 5.40 | Tumour | Healthy | Putative uncharacterized protein | tr\|Q3U944\|Q3U944_MOUSE |
| 5.39 | Healthy | Tumour | N-acetylglucosaminyl-phosphatidylinositol biosynthetic protein | sp\|Q64323\|PIGA_MOUSE |
| 5.32 | Healthy | Tumour | Glutathione peroxidase 3 | sp\|P46412\|GPX3_MOUSE;tr\|D3Z2Y7\|D3Z2Y7_MOUSE |
| 5.28 | Healthy | Tumour | Protein Ces1a | tr\|E9PYP1\|E9PYP1_MOUSE |
| 5.27 | Tumour | Healthy | 7-alpha-hydroxycholest-4-en-3-one 12-alpha-hydroxylase | sp\|O88962\|CP8B1_MOUSE |
| 5.23 | Tumour | Healthy | Syntaxin-binding protein 3 | sp\|Q60770\|STXB3_MOUSE |
| 5.12 | Tumour | Healthy | Bile acyl-CoA synthetase | sp\|Q4LDG0\|S27A5_MOUSE |
| 5.10 | Tumour | Healthy | Ribosomal protein L7A | tr\|Q6P1A9\|Q6P1A9_MOUSE |
| 5.07 | Healthy | Tumour | 60S ribosomal protein L18 (Fragment) | tr\|G3UYV6\|G3UYV6_MOUSE |

FIG. 4(b)

| Max fold change | Highest mean condition | Lowest mean condition | Description | Accession |
|---|---|---|---|---|
| Infinity | Healthy | Tumour | Beta-actin (Fragment) | tr\|A1E281\|A1E281_MOUSE |
| 50.25 | Tumour | Healthy | Hemoglobin subunit beta-2 | sp\|P02089\|HBB2_MOUSE;tr\|A8DV59\|A8DV59_MOUSE;tr\|D4N6N2\|D4N6N2_MUSMC |
| 43.39 | Healthy | Tumour | Fibrinogen alpha chain | sp\|E9PV24\|FIBA_MOUSE |
| 42.75 | Healthy | Tumour | Putative uncharacterized protein | tr\|Q3UEM7\|Q3UEM7_MOUSE |
| 17.95 | Healthy | Tumour | Cytochrome P450 2F2 | sp\|P33267\|CP2F2_MOUSE |
| 17.24 | Healthy | Tumour | Fibrinogen, B beta polypeptide, isoform CRA_a | tr\|Q3TGR2\|Q3TGR2_MOUSE |
| 14.18 | Healthy | Tumour | Keratin (Fragment) | tr\|Q61764\|Q61764_MOUSE |
| 12.48 | Healthy | Tumour | Precursor polypeptide (AA -10 to 121) (413 is 1st base in codon) (Fragment) | tr\|A2NV19\|A2NV19_MOUSE |
| 12.23 | Tumour | Healthy | Alpha-1-antitrypsin 1-1 | sp\|P07758\|A1AT1_MOUSE;tr\|D3YZL0\|D3YZL0_MOUSE |
| 11.36 | Healthy | Tumour | Protein Ighv1-20 | tr\|A0A075B5U6\|A0A075B5U6_MOUSE |
| 9.86 | Healthy | Tumour | Keratin, type II cytoskeletal 4 | sp\|P07744\|K2C4_MOUSE |
| 9.69 | Healthy | Tumour | Putative uncharacterized protein | tr\|Q9DCD9\|Q9DCD9_MOUSE |
| 9.31 | Tumour | Healthy | Carboxypeptidase Q | sp\|Q9WVJ3\|CBPQ_MOUSE |
| 9.13 | Healthy | Tumour | EP3-31 light chain variable region (Fragment) | tr\|B5UB71\|B5UB71_MOUSE |
| 8.87 | Tumour | Healthy | Ugt2b36 protein | tr\|B7ZP03\|B7ZP03_MOUSE;tr\|D3YUP6\|D3YUP6_MOUSE |
| 8.06 | Healthy | Tumour | Protein Ighv1-85 | tr\|A0A075B5Y6\|A0A075B5Y6_MOUSE |
| 8.02 | Healthy | Tumour | Beta-actin-like protein 2 | sp\|Q8BFZ3\|ACTBL_MOUSE |
| 7.96 | Healthy | Tumour | Protein Igkv8-24 | tr\|A0A087WNJ5\|A0A087WNJ5_MOUSE;tr\|A2N1N1\|A2N1N1_MOUSE |
| 7.50 | Healthy | Tumour | VH7183-DSP2-JH3-CH1 protein (Fragment) | tr\|Q65ZL8\|Q65ZL8_MOUSE |
| 7.41 | Healthy | Tumour | Heat shock protein 90kDa beta (Grp94), member 1 | tr\|Q3UAD6\|Q3UAD6_MOUSE;tr\|D3Z1R1\|D3Z1R1_MOUSE;tr\|F7C312\|F7C312_MOUSE;tr\|Q3TUD6\|Q3TUD6_MOUSE;tr\|Q8C2R2\|Q8C2R2_MOUSE;tr\|Q9CW12\|Q9CW12_MOUSE |
| 6.98 | Healthy | Tumour | Ankyrin-1 | tr\|G3UY11\|G3UY11_MOUSE |
| 6.95 | Tumour | Healthy | Igh protein | tr\|Q6PIP8\|Q6PIP8_MOUSE;sp\|P01863\|GCAA_MOUSE |
| 6.75 | Healthy | Tumour | Cytochrome P450 2D9 | sp\|P11714\|CP2D9_MOUSE |
| 6.68 | Healthy | Tumour | Tubulin alpha-4A chain (Fragment) | tr\|A0A087WQS4\|A0A087WQS4_MOUSE |
| 6.63 | Tumour | Healthy | Ig kappa chain V-VI region XRPC 44 | sp\|P01675\|KV6A1_MOUSE |
| 6.21 | Healthy | Tumour | Skeletal muscle alpha-actin mRNA (Fragment) | tr\|Q61264\|Q61264_MOUSE |
| 5.92 | Tumour | Healthy | LOC676837 protein | tr\|B2RY37\|B2RY37_MOUSE |
| 5.88 | Tumour | Healthy | Putative uncharacterized protein | tr\|Q3TK73\|Q3TK73_MOUSE |
| 5.61 | Healthy | Tumour | Moesin | sp\|P26041\|MOES_MOUSE;tr\|Q05DU4\|Q05DU4_MOUSE;tr\|Q3UF33\|Q3UF33_MOUSE |
| 5.59 | Tumour | Healthy | Putative uncharacterized protein | tr\|Q8BK73\|Q8BK73_MOUSE |
| 5.41 | Tumour | Healthy | Erythrocyte band 7 integral membrane protein | sp\|P54116\|STOM_MOUSE;tr\|Q8BPA1\|Q8BPA1_MOUSE |
| 5.37 | Healthy | Tumour | Ankyrin-1 | tr\|D3Z5M4\|D3Z5M4_MOUSE;tr\|B7ZW98\|B7ZW98_MOUSE;tr\|F7D1P5\|F7D1P5_MOUSE |
| 5.25 | Tumour | Healthy | Transient receptor potential cation channel subfamily M member 8 | sp\|Q8R4D5\|TRPM8_MOUSE |

FIG. 5(a)

| Max fold change | Highest mean condition | Lowest mean condition | Description | Accession |
|---|---|---|---|---|
| Infinity | Tumour | Healthy | Putative uncharacterized protein | tr\|Q3V2B9\|Q3V2B9_MOUSE |
| 144.58 | Healthy | Tumour | Putative uncharacterized protein (Fragment) | tr\|Q9CUN8\|Q9CUN8_MOUSE |
| 69.50 | Healthy | Tumour | Ig kappa chain V-III region PC 2154 | sp\|P01674\|KV3AM_MOUSE |
| 59.33 | Tumour | Healthy | Actin, cytoplasmic 2 (Fragment) | tr\|G3UZ07\|G3UZ07_MOUSE |
| 51.27 | Healthy | Tumour | Putative uncharacterized protein | tr\|Q3V3W7\|Q3V3W7_MOUSE;tr\|Q3TQH1\|Q3TQH1_MOUSE |
| 47.96 | Healthy | Tumour | Putative uncharacterized protein | tr\|Q3UER8\|Q3UER8_MOUSE |
| 47.04 | Healthy | Tumour | Coagulation factor XIII, beta subunit | tr\|Q8K0W0\|Q8K0W0_MOUSE |
| 41.08 | Healthy | Tumour | Putative uncharacterized protein | tr\|Q3TB69\|Q3TB69_MOUSE |
| 41.07 | Healthy | Tumour | Translocation protein SEC62 | sp\|Q8BU14\|SEC62_MOUSE |
| 38.82 | Healthy | Tumour | Fibrinogen alpha chain | sp\|E9PV24\|FIBA_MOUSE |
| 28.06 | Healthy | Tumour | Putative uncharacterized protein (Fragment) | tr\|Q3UAS8\|Q3UAS8_MOUSE |
| 27.46 | Healthy | Tumour | Fibrinogen, B beta polypeptide, isoform CRA_a | tr\|Q3TGR2\|Q3TGR2_MOUSE |
| 25.57 | Tumour | Healthy | NAD(P) dependent steroid dehydrogenase-like | tr\|Q8VE30\|Q8VE30_MOUSE |
| 25.20 | Healthy | Tumour | Signal peptide peptidase-like 2A | sp\|Q9JJF9\|SPP2A_MOUSE |
| 24.18 | Tumour | Healthy | Steryl-sulfatase | sp\|P50427\|STS_MOUSE |
| 23.09 | Tumour | Healthy | Peptidyl-prolyl cis-trans isomerase FKBP11 | sp\|Q9D1M7\|FKB11_MOUSE |
| 22.20 | Tumour | Healthy | Bax inhibitor 1 (Fragment) | tr\|E0CX98\|E0CX98_MOUSE |
| 21.52 | Tumour | Healthy | MCG140784 | tr\|Q792Z1\|Q792Z1_MOUSE |
| 20.93 | Healthy | Tumour | 26S protease regulatory subunit 6A | tr\|A2AGN7\|A2AGN7_MOUSE |
| 19.73 | Tumour | Healthy | Pterin-mimicking anti-idiotope heavy chain variable region (Fragment) | tr\|Q920E7\|Q920E7_MOUSE |
| 19.10 | Tumour | Healthy | Igh protein | tr\|Q3KQK2\|Q3KQK2_MOUSE |
| 17.65 | Tumour | Healthy | 3 beta-hydroxysteroid dehydrogenase type 5 | sp\|Q61694\|3BHS5_MOUSE |
| 17.50 | Tumour | Healthy | 3 beta-hydroxysteroid dehydrogenase/Delta 5-->4-isomerase type 6 OS=Mus musculus GN=Hsd3b6 PE=2 SV=4 | sp\|O35469\|3BHS6_MOUSE |
| 16.91 | Tumour | Healthy | Fn1 protein (Fragment) | tr\|Q99KD0\|Q99KD0_MOUSE |
| 15.06 | Tumour | Healthy | Microsomal glutathione S-transferase 1 | tr\|E9QJW0\|E9QJW0_MOUSE;tr\|D3YVR3\|D3YVR3_MOUSE |
| 13.89 | Tumour | Healthy | Very-long-chain (3R)-3-hydroxyacyl-CoA dehydratase 2 | sp\|Q9D3B1\|HACD2_MOUSE |
| 13.71 | Tumour | Healthy | Protein Igkv4-86 | tr\|A0A075B5L5\|A0A075B5L5_MOUSE |
| 13.26 | Healthy | Tumour | Complement component C8 beta chain | sp\|Q8BH35\|CO8B_MOUSE |
| 13.22 | Healthy | Tumour | Keratin (Fragment) | tr\|Q61764\|Q61764_MOUSE |
| 13.10 | Healthy | Tumour | Annexin (Fragment) | tr\|F7ANV6\|F7ANV6_MOUSE |
| 13.00 | Tumour | Healthy | Cytochrome c oxidase subunit 2 | tr\|A0A023J6F3\|A0A023J6F3_MOUSE;tr\|A0A023J5Y1\|A0A023J5Y1_MOUSE |
| 12.02 | Tumour | Healthy | BTB (POZ) domain containing 1 | tr\|Q5M8N6\|Q5M8N6_MOUSE |
| 11.79 | Tumour | Healthy | Putative uncharacterized protein (Fragment) | tr\|Q3U3J9\|Q3U3J9_MOUSE |
| 11.54 | Tumour | Healthy | Treml1 protein | tr\|B7ZNI7\|B7ZNI7_MOUSE |
| 11.42 | Tumour | Healthy | Putative uncharacterized protein | tr\|Q9CY59\|Q9CY59_MOUSE |
| 11.42 | Healthy | Tumour | Dolichyl-diphosphooligosaccharide--protein glycosyltransferase subunit STT3B OS=Mus musculus GN=Stt3b PE=1 SV=2 | sp\|Q3TDQ1\|STT3B_MOUSE |
| 11.01 | Healthy | Tumour | Plectin | sp\|Q9QXS1\|PLEC_MOUSE |
| 10.41 | Tumour | Healthy | Cytochrome P450 2D9 | sp\|P11714\|CP2D9_MOUSE |
| 10.39 | Healthy | Tumour | Guanine nucleotide-binding protein subunit alpha-12 | sp\|P27600\|GNA12_MOUSE;tr\|Q2NKI3\|Q2NKI3_MOUSE |
| 10.38 | Tumour | Healthy | Membrane protein, palmitoylated | tr\|Q542P4\|Q542P4_MOUSE;tr\|B7ZCL9\|B7ZCL9_MOUSE;tr\|B7ZCM0\|B7ZCM0_MOUSE;tr\|Q3THA8\|Q3THA8_MOUSE |
| 10.20 | Tumour | Healthy | Serum amyloid A-4 protein | sp\|P31532\|SAA4_MOUSE |
| 10.13 | Tumour | Healthy | Glycine N-methyltransferase | tr\|Q5I0T9\|Q5I0T9_MOUSE |
| 10.04 | Tumour | Healthy | Cytochrome P450, family 2, subfamily b, polypeptide 13 | tr\|A6H6J2\|A6H6J2_MOUSE |
| 9.95 | Tumour | Healthy | Cytochrome P450 CYP2C44 OS=Mus musculus GN=Cyp2c44 PE=2 SV=1 | tr\|Q6IEF7\|Q6IEF7_MOUSE;tr\|Q3UEM4\|Q3UEM4_MOUSE;tr\|Q8CIE7\|Q8CIE7_MOUSE |
| 9.92 | Healthy | Tumour | TBC1 domain family member 8B | sp\|A3KGB4\|TBC8B_MOUSE |
| 9.87 | Tumour | Healthy | Putative uncharacterized protein | tr\|Q3UGZ4\|Q3UGZ4_MOUSE;tr\|Q68FM2\|Q68FM2_MOUSE |
| 9.87 | Tumour | Healthy | MKIAA0302 protein (Fragment) | tr\|Q6A087\|Q6A087_MOUSE |

FIG. 5(b)A

| | | | | |
|---|---|---|---|---|
| 9.81 | Tumour | Healthy | Signal sequence receptor, delta, isoform CRA_b | tr\|Q3TVJ8\|Q3TVJ8_MOUSE |
| 9.69 | Tumour | Healthy | Cis-retinol androgen dehydrogenase 1 | tr\|O54909\|O54909_MOUSE |
| 9.53 | Tumour | Healthy | Polymerase I and transcript release factor | sp\|O54724\|PTRF_MOUSE;tr\|Q3TER0\|Q3TER0_MOUSE |
| 9.48 | Tumour | Healthy | Carbonic anhydrase 3 | sp\|P16015\|CAH3_MOUSE |
| 9.45 | Tumour | Healthy | Dimethylaniline monooxygenase [N-oxide-forming] 1 | sp\|P50285\|FMO1_MOUSE;tr\|D3Z0T2\|D3Z0T2_MOUSE;tr\|Q3UNX7\|Q3UNX7_MOUSE;tr\|Q8C9C1\|Q8C9C1_MOUSE |
| 9.09 | Tumour | Healthy | Solute carrier family 22 member 18 | sp\|Q78KK3\|S22AI_MOUSE |
| 9.05 | Tumour | Healthy | Protein Cyp2c68 | tr\|K7N6C2\|K7N6C2_MOUSE |
| 8.96 | Tumour | Healthy | Putative uncharacterized protein | tr\|Q3TEK2\|Q3TEK2_MOUSE |
| 8.92 | Tumour | Healthy | Delta(14)-sterol reductase | tr\|E9Q4M8\|E9Q4M8_MOUSE |
| 8.74 | Tumour | Healthy | Putative uncharacterized protein | tr\|Q3TDT8\|Q3TDT8_MOUSE |
| 8.63 | Tumour | Healthy | Putative uncharacterized protein | tr\|Q3U7E6\|Q3U7E6_MOUSE;tr\|E0CXD9\|E0CXD9_MOUSE |
| 8.54 | Tumour | Healthy | Sulfotransferase | tr\|Q9R1S5\|Q9R1S5_MOUSE |
| 8.52 | Healthy | Tumour | Cytoplasmic dynein heavy chain (Fragment) | tr\|O08821\|O08821_MOUSE |
| 8.50 | Healthy | Tumour | Retinol-binding protein 3 | sp\|P49194\|RET3_MOUSE |
| 8.38 | Tumour | Healthy | Iodotyrosine dehalogenase 1 | sp\|Q9DCX8\|IYD1_MOUSE |
| 8.28 | Tumour | Healthy | Myadm protein | tr\|Q0VE46\|Q0VE46_MOUSE |
| 8.20 | Tumour | Healthy | Putative uncharacterized protein | tr\|Q3TXE5\|Q3TXE5_MOUSE |
| 8.11 | Tumour | Healthy | Fructose-1,6-bisphosphatase 1 OS=Mus musculus GN=Fbp1 PE=4 SV=1 | tr\|E9Q0T7\|E9Q0T7_MOUSE |
| 7.85 | Tumour | Healthy | Cytochrome P450 2C29 | sp\|Q64458\|CP2CT_MOUSE;tr\|H3BLM0\|H3BLM0_MOUSE |
| 7.69 | Tumour | Healthy | Putative uncharacterized protein | tr\|Q3TPA9\|Q3TPA9_MOUSE |
| 7.52 | Healthy | Tumour | Ankyrin-2 | sp\|Q8C8R3\|ANK2_MOUSE |
| 7.48 | Tumour | Healthy | Solute carrier family 43 member 3 | sp\|A2AVZ9\|S43A3_MOUSE |
| 7.41 | Tumour | Healthy | Basal cell adhesion molecule | sp\|Q9R069\|BCAM_MOUSE |
| 7.40 | Tumour | Healthy | Duffy blood group antigen | tr\|Q7TSL2\|Q7TSL2_MOUSE |
| 7.40 | Tumour | Healthy | Protein Ugt2b34 | tr\|Q8K154\|Q8K154_MOUSE;tr\|E9PZ30\|E9PZ30_MOUSE |
| 7.38 | Tumour | Healthy | CSC1-like protein 1 | sp\|Q91YT8\|CSCL1_MOUSE |
| 7.37 | Tumour | Healthy | Uncharacterized protein | tr\|D3Z6R0\|D3Z6R0_MOUSE |
| 7.36 | Tumour | Healthy | UDP-glucuronosyltransferase 2A3 | sp\|Q8BWQ1\|UD2A3_MOUSE |
| 7.26 | Healthy | Tumour | Keratin, type II cytoskeletal 4 | sp\|P07744\|K2C4_MOUSE |
| 7.11 | Healthy | Tumour | Ephrin B1, isoform CRA_a | tr\|Q544L9\|Q544L9_MOUSE |
| 7.03 | Healthy | Tumour | ADP-ribosylation factor 5 | sp\|P84084\|ARF5_MOUSE |
| 7.01 | Tumour | Healthy | Hemoglobin subunit beta-2 | sp\|P02089\|HBB2_MOUSE;tr\|A8DV59\|A8DV59_MOUSE;tr\|D4N6N2\|D4N6N2_MUSMC |
| 6.98 | Tumour | Healthy | 3 beta-hydroxysteroid dehydrogenase type 7 | sp\|Q9EQC1\|3BHS7_MOUSE |
| 6.92 | Healthy | Tumour | Gamma heavy chain variable region (Fragment) | tr\|Q5F2I8\|Q5F2I8_MOUSE |
| 6.90 | Healthy | Tumour | DNA damage-binding protein 1 | sp\|Q3U1J4\|DDB1_MOUSE |
| 6.85 | Tumour | Healthy | Chloride intracellular channel protein 3 | tr\|A2AJ28\|A2AJ28_MOUSE |
| 6.82 | Tumour | Healthy | Putative uncharacterized protein | tr\|Q9DC85\|Q9DC85_MOUSE |
| 6.81 | Tumour | Healthy | 3-keto-steroid reductase | tr\|Q8C5N9\|Q8C5N9_MOUSE |
| 6.79 | Tumour | Healthy | Methyltransferase-like protein 7B | sp\|Q9DD20\|MET7B_MOUSE |
| 6.78 | Tumour | Healthy | Ankyrin-1 | tr\|G8JL84\|G8JL84_MOUSE;sp\|Q02357\|ANK1_MOUSE;tr\|D6RJ51\|D6RJ51_MOUSE;tr\|F7D1P5\|F7D1P5_MOUSE;tr\|Q61304\|Q61304_MOUSE |
| 6.76 | Tumour | Healthy | Putative uncharacterized protein | tr\|Q3UF03\|Q3UF03_MOUSE |
| 6.75 | Tumour | Healthy | Putative uncharacterized protein | tr\|Q3TFP8\|Q3TFP8_MOUSE |
| 6.64 | Tumour | Healthy | Glycolipid transfer protein domain-containing protein 2 | sp\|Q8K0R6\|GLTD2_MOUSE |
| 6.58 | Healthy | Tumour | Protein Ahnak | tr\|E9Q616\|E9Q616_MOUSE;tr\|A0JLR7\|A0JLR7_MOUSE |
| 6.58 | Healthy | Tumour | AHNAK (Fragment) | tr\|Q6UL10\|Q6UL10_MOUSE;tr\|Q61484\|Q61484_MOUSE |
| 6.54 | Healthy | Tumour | Cytochrome P450 2A5 (Fragment) | tr\|F6SHL3\|F6SHL3_MOUSE |
| 6.49 | Healthy | Tumour | Protein Ighv7-1 | tr\|A0A075B5S2\|A0A075B5S2_MOUSE |
| 6.48 | Tumour | Healthy | Collagen alpha-1(XIV) chain (Fragment) | tr\|F7D5Y4\|F7D5Y4_MOUSE |
| 6.43 | Healthy | Tumour | 60S ribosomal protein L7 (Fragment) | tr\|F6XI62\|F6XI62_MOUSE |
| 6.41 | Healthy | Tumour | Protein 9530053A07Rik | tr\|E9PVG8\|E9PVG8_MOUSE |
| 6.39 | Tumour | Healthy | Probable N-acetyltransferase CML2 | sp\|Q8CHQ9\|CML02_MOUSE |
| 6.35 | Tumour | Healthy | Transmembrane 9 superfamily member 4 | sp\|Q8BH24\|TM9S4_MOUSE |

FIG. 5(b)B

| | | | | |
|---|---|---|---|---|
| 6.28 | Healthy | Tumour | Putative uncharacterized protein | tr\|Q9CY10\|Q9CY10_MOUSE |
| 6.22 | Tumour | Healthy | Annexin A5 OS=Mus musculus GN=Anxa5 PE=1 SV=1 | sp\|P48036\|ANXA5_MOUSE |
| 6.19 | Healthy | Tumour | von Willebrand factor OS=Mus musculus GN=Vwf PE=1 SV=2 | sp\|Q8CIZ8\|VWF_MOUSE |
| 6.12 | Tumour | Healthy | Uncharacterized protein OS=Mus musculus GN=Gm5422 PE=4 SV=1 | tr\|J3KMQ2\|J3KMQ2_MOUSE |
| 6.12 | Tumour | Healthy | Solute carrier family 2, facilitated glucose transporter member 2 OS=Mus musculus GN=Slc2a2 PE=1 SV=3 | sp\|P14246\|GTR2_MOUSE |
| 6.07 | Healthy | Tumour | Vacuolar protein sorting-associated protein 13A | sp\|Q5H8C4\|VP13A_MOUSE |
| 6.06 | Tumour | Healthy | Cytochrome P450 2D26 | sp\|Q8CIM7\|CP2DQ_MOUSE |
| 6.02 | Tumour | Healthy | Putative uncharacterized protein | tr\|Q3TJK3\|Q3TJK3_MOUSE |
| 5.98 | Tumour | Healthy | Putative uncharacterized protein | tr\|Q3TK73\|Q3TK73_MOUSE |
| 5.96 | Tumour | Healthy | IgM heavy chain VDJ region (Fragment) | tr\|X5J5L2\|X5J5L2_MOUSE |
| 5.90 | Healthy | Tumour | Alpha-2-macroglobulin (Fragment) OS=Mus musculus GN=Pzp PE=4 SV=1 | tr\|D3YUI3\|D3YUI3_MOUSE |
| 5.89 | Healthy | Tumour | Mannose binding lectin (C), isoform CRA_b | tr\|Q3UEK1\|Q3UEK1_MOUSE |
| 5.87 | Tumour | Healthy | Putative uncharacterized protein | tr\|Q3TV47\|Q3TV47_MOUSE |
| 5.85 | Tumour | Healthy | UDP-glucuronosyltransferase 3A2 | sp\|Q8JZZ0\|UD3A2_MOUSE |
| 5.83 | Healthy | Tumour | Eukaryotic translation initiation factor 3 subunit C | sp\|Q8R1B4\|EIF3C_MOUSE |
| 5.79 | Tumour | Healthy | Ras-related protein Rab-1A | sp\|P62821\|RAB1A_MOUSE;tr\|Q3UB66\|Q3UB66_MOUSE |
| 5.77 | Tumour | Healthy | 17-beta-hydroxysteroid dehydrogenase 13 | tr\|A8Y5N4\|A8Y5N4_MOUSE |
| 5.76 | Tumour | Healthy | UDP-glucuronosyltransferase 1-6 | sp\|Q64435\|UD16_MOUSE |
| 5.73 | Tumour | Healthy | Long-chain-fatty-acid--CoA ligase 5 | sp\|Q8JZR0\|ACSL5_MOUSE;tr\|Q9D9S0\|Q9D9S0_MOUSE |
| 5.68 | Tumour | Healthy | Ig kappa chain V-III region PC 2413 | sp\|P01657\|KV3AS_MOUSE |
| 5.68 | Healthy | Tumour | RAB14 protein variant | tr\|Q50HX1\|Q50HX1_MOUSE |
| 5.59 | Healthy | Tumour | Mesothelin | sp\|Q61468\|MSLN_MOUSE |
| 5.57 | Tumour | Healthy | Anti-VIPase light chain variable region (Fragment) | tr\|Q8K1F2\|Q8K1F2_MOUSE |
| 5.54 | Healthy | Tumour | Cytoplasmic dynein 1 heavy chain 1 | sp\|Q9JHU4\|DYHC1_MOUSE;tr\|Q3UA73\|Q3UA73_MOUSE;tr\|Q80U36\|Q80U36_MOUSE;tr\|Q8C6T5\|Q8C6T5_MOUSE |
| 5.51 | Tumour | Healthy | 3 beta-hydroxysteroid dehydrogenase/Delta 5-->4-isomerase type 3 | sp\|P26150\|3BHS3_MOUSE;tr\|B1ARN9\|B1ARN9_MOUSE |
| 5.48 | Healthy | Tumour | Ankyrin-1 (Fragment) | tr\|G3UXF4\|G3UXF4_MOUSE |
| 5.46 | Tumour | Healthy | 14-3-3 protein zeta/delta | sp\|P63101\|1433Z_MOUSE |
| 5.45 | Healthy | Tumour | Ig kappa chain V-IV region S107B | sp\|P01680\|KV4A1_MOUSE |
| 5.40 | Tumour | Healthy | Igh protein | tr\|Q5U472\|Q5U472_MOUSE |
| 5.39 | Tumour | Healthy | NADPH--cytochrome P450 reductase | sp\|P37040\|NCPR_MOUSE;tr\|E9PVT9\|E9PVT9_MOUSE;tr\|E9Q997\|E9Q997_MOUSE;tr\|F6R7H8\|F6R7H8_MOUSE;tr\|Q05DV1\|Q05DV1_MOUSE |
| 5.37 | Healthy | Tumour | Vesicle transport through interaction with t-SNAREs 1B homolog | tr\|Q91XH6\|Q91XH6_MOUSE |
| 5.32 | Tumour | Healthy | Vitronectin | sp\|P29788\|VTNC_MOUSE |
| 5.31 | Tumour | Healthy | Cytochrome P450 2B9 | sp\|P12790\|CP2B9_MOUSE |
| 5.29 | Tumour | Healthy | Cytochrome P450 4A14 | sp\|O35728\|CP4AE_MOUSE |
| 5.28 | Tumour | Healthy | Putative uncharacterized protein | tr\|Q3UEJ7\|Q3UEJ7_MOUSE |
| 5.27 | Healthy | Tumour | Ig kappa chain V-VI region XRPC 44 | sp\|P01675\|KV6A1_MOUSE |
| 5.25 | Tumour | Healthy | Sarcoplasmic/endoplasmic reticulum calcium ATPase 1 | sp\|Q8R429\|AT2A1_MOUSE;tr\|Q3V1C4\|Q3V1C4_MOUSE |
| 5.23 | Healthy | Tumour | Serine (Or cysteine) peptidase inhibitor, clade F, member 2, isoform CRA_c | tr\|Q5ND36\|Q5ND36_MOUSE;tr\|E9PXE0\|E9PXE0_MOUSE;tr\|Q5ND35\|Q5ND35_MOUSE |
| 5.23 | Healthy | Tumour | Heat shock-related 70 kDa protein 2 | sp\|P17156\|HSP72_MOUSE |
| 5.21 | Tumour | Healthy | Transmembrane channel-like protein | tr\|B1ATB3\|B1ATB3_MOUSE |
| 5.21 | Tumour | Healthy | Hsd17b2 protein | tr\|Q91X35\|Q91X35_MOUSE |

FIG. 5(b)C

| | | | | |
|---|---|---|---|---|
| 5.20 | Tumour | Healthy | Myosin-9 OS=Mus musculus GN=Myh9 PE=1 SV=4 | sp\|Q8VDD5\|MYH9_MOUSE;tr\|A2VCK0\|A2VCK0_MOUSE;tr\|Q7TQJ6\|Q7TQJ6_MOUSE;tr\|Q811J9\|Q811J9_MOUSE;tr\|Q8BIE2\|Q8BIE2_MOUSE |
| 5.19 | Healthy | Tumour | Putative uncharacterized protein | tr\|Q3UHL7\|Q3UHL7_MOUSE;tr\|Q3UR38\|Q3UR38_MOUSE |
| 5.14 | Tumour | Healthy | Putative uncharacterized protein | tr\|Q3UYU1\|Q3UYU1_MOUSE |
| 5.14 | Tumour | Healthy | Regucalcin | sp\|Q64374\|RGN_MOUSE |
| 5.12 | Healthy | Tumour | Igh protein | tr\|Q4V9Z4\|Q4V9Z4_MOUSE |
| 5.10 | Tumour | Healthy | MCG17387, isoform CRA_a | tr\|Q5FWB6\|Q5FWB6_MOUSE;tr\|D3YVM5\|D3YVM5_MOUSE |
| 5.06 | Tumour | Healthy | Cytochrome b-5, isoform CRA_a | tr\|G5E850\|G5E850_MOUSE |
| 5.05 | Tumour | Healthy | Tubulin alpha-4A chain | sp\|P68368\|TBA4A_MOUSE |
| 5.04 | Healthy | Tumour | Aminopeptidase A | tr\|Q52JJ6\|Q52JJ6_MOUSE |
| 5.03 | Tumour | Healthy | Hemoglobin beta chain subunit | tr\|B1Q450\|B1Q450_MOUSE |
| 5.02 | Healthy | Tumour | Coagulation factor X | tr\|Q3TBR2\|Q3TBR2_MOUSE |
| 5.01 | Tumour | Healthy | Starch-binding domain-containing protein 1 | sp\|Q8C7E7\|STBD1_MOUSE |
| 5.00 | Tumour | Healthy | Oncoprotein-induced transcript 3 protein | sp\|Q8R4V5\|OIT3_MOUSE |

FIG. 5(b)D

| Rank | RPA% | Plasma Proteins by Abundance |
|---|---|---|
| 1 | 17.38 | Serum Albumin |
| 2 | 3.92 | monoclonal antibody CR8033 light chain |
| 3 | 3.84 | Fab light chain |
| 4 | 3.77 | light chain O12/KAPPA |
| 5 | 3.59 | Putative uncharacterized protein DKFZp686C11235 |
| 6 | 3.48 | MSL-109 Light Chain |
| 7 | 3.48 | 679-14-14E06 Fab fragment light chain |
| 8 | 3.41 | B3 (IGKV4-1) light chain |
| 9 | 2.88 | IGH protein |
| 10 | 2.79 | cDNA FLJ78387 |

| | Rank | RPA% | Identified Proteins | Accession Number |
|---|---|---|---|---|
| Patient 1 | 1 | 7.68 | Full-length cDNA clone CS0DD006YL02 of Neuroblastoma | Q86TT1_HUMAN |
| | 2 | 5.42 | Ig mu chain C region(A0A087X2C0) | A0A087X2C0_HUMAN |
| | 3 | 5.17 | Ig mu chain C region(A0A087WYJ9) | A0A087WYJ9_HUMAN |
| | 4 | 5.17 | Fibrinogen beta chain | FIBB_HUMAN (+1) |
| | 5 | 3.49 | Alpha-2-macroglobulin | A2MG_HUMAN |
| | 6 | 3.25 | Fibrinogen alpha chain | FIBA_HUMAN |
| | 7 | 2.55 | C4b-binding protein alpha chain | C4BPA_HUMAN |
| | 8 | 1.92 | Fibrinogen gamma chain | FIBG_HUMAN |
| | 9 | 1.84 | Protein IGHV3-72 | A0A087WW89_HUMAN |
| | 10 | 1.65 | Haptoglobin | H0Y300_HUMAN |
| Patient 2 | 1 | 5.47 | Serum albumin | ALBU_HUMAN |
| | 2 | 4.90 | Full-length cDNA clone CS0DD006YL02 of Neuroblastoma | Q86TT1_HUMAN |
| | 3 | 3.95 | Fibrinogen beta chain | FIBB_HUMAN (+1) |
| | 4 | 3.53 | Ig mu chain C region(A0A087X2C0) | A0A087X2C0_HUMAN |
| | 5 | 3.40 | Ig mu chain C region(A0A087WYJ9) | A0A087WYJ9_HUMAN |
| | 6 | 3.12 | Alpha-2-macroglobulin | A2MG_HUMAN |
| | 7 | 2.70 | Fibrinogen alpha chain | FIBA_HUMAN |
| | 8 | 2.33 | Putative uncharacterized protein DKFZp686C11235 | Q6MZV7_HUMAN |
| | 9 | 2.10 | C4b-binding protein alpha chain | C4BPA_HUMAN |
| | 10 | 1.91 | Fibrinogen gamma chain | FIBG_HUMAN |
| Patient 3 | 1 | 6.91 | Full-length cDNA clone CS0DD006YL02 of Neuroblastoma | Q86TT1_HUMAN |
| | 2 | 4.81 | Ig mu chain C region(A0A087X2C0) | A0A087X2C0_HUMAN |
| | 3 | 4.72 | Serum albumin | ALBU_HUMAN |
| | 4 | 4.66 | Ig mu chain C region(A0A087WYJ9) | A0A087WYJ9_HUMAN |
| | 5 | 3.60 | Fibrinogen beta chain | FIBB_HUMAN (+1) |
| | 6 | 3.28 | Fibrinogen alpha chain | FIBA_HUMAN |
| | 7 | 2.38 | Putative uncharacterized protein DKFZp686C11235 | Q6MZV7_HUMAN |
| | 8 | 2.22 | Fibrinogen gamma chain | FIBG_HUMAN |
| | 9 | 2.11 | IGH protein | Q6GMX6_HUMAN |
| | 10 | 2.03 | Ig gamma-1 chain C region | A0A087WV47_HUMAN (+1) |
| Patient 4 | 1 | 7.99 | Full-length cDNA clone CS0DD006YL02 of Neuroblastoma | Q86TT1_HUMAN |
| | 2 | 5.69 | Ig mu chain C region(A0A087X2C0) | A0A087X2C0_HUMAN |
| | 3 | 4.68 | Ig mu heavy chain disease protein | MUCB_HUMAN |
| | 4 | 4.55 | Alpha-2-macroglobulin | A2MG_HUMAN |
| | 5 | 3.64 | Lipoprotein B (Fragment) | S5FLF7_HUMAN |
| | 6 | 3.42 | APOB protein | Q7Z7Q0_HUMAN |
| | 7 | 3.37 | Apolipoprotein B (Including Ag(X) antigen) | C0JYY2_HUMAN |
| | 8 | 3.05 | Fibrinogen beta chain | FIBB_HUMAN (+1) |
| | 9 | 2.77 | Fibrinogen alpha chain | FIBA_HUMAN |
| | 10 | 2.68 | Apolipoprotein B variant (Fragment) | Q59HB3_HUMAN |
| Patient 5 | 1 | 12.44 | Full-length cDNA clone CS0DD006YL02 of Neuroblastoma | Q86TT1_HUMAN |
| | 2 | 8.99 | Ig mu chain C region(A0A087X2C0) | A0A087X2C0_HUMAN |
| | 3 | 8.65 | Ig mu chain C region(A0A087WYJ9) | A0A087WYJ9_HUMAN |
| | 4 | 3.79 | Apolipoprotein B (Including Ag(X) antigen) | C0JYY2_HUMAN |
| | 5 | 3.79 | APOB protein | Q7Z7Q0_HUMAN |
| | 6 | 3.48 | Alpha-2-macroglobulin | A2MG_HUMAN |
| | 7 | 2.85 | Protein IGHV3-72 | A0A087WW89_HUMAN |
| | 8 | 2.28 | Immunglobulin heavy chain variable region (Fragment) | Q0ZCH9_HUMAN |
| | 9 | 1.96 | Fibrinogen alpha chain | FIBA_HUMAN |
| | 10 | 1.95 | C4b-binding protein alpha chain | C4BPA_HUMAN |
| Patient 6 | 1 | 8.00 | Full-length cDNA clone CS0DD006YL02 of Neuroblastoma | Q86TT1_HUMAN |
| | 2 | 5.76 | Ig mu chain C region(A0A087X2C0) | A0A087X2C0_HUMAN |
| | 3 | 5.46 | Ig mu chain C region(A0A087WYJ9) | A0A087WYJ9_HUMAN |
| | 4 | 4.92 | APOB protein | Q7Z7Q0_HUMAN |
| | 5 | 4.52 | Apolipoprotein B (Including Ag(X) antigen) | C0JYY2_HUMAN |
| | 6 | 4.45 | Alpha-2-macroglobulin | A2MG_HUMAN |
| | 7 | 3.93 | Fibrinogen alpha chain | FIBA_HUMAN |
| | 8 | 3.43 | Fibrinogen beta chain | FIBB_HUMAN (+1) |
| | 9 | 2.00 | Actin, cytoplasmic 2 | ACTG_HUMAN (+1) |
| | 10 | 1.66 | C4b-binding protein alpha chain | C4BPA_HUMAN |

FIG. 9

| Rank | RPA% (Mean) | Identified Proteins | Accession Number |
|---|---|---|---|
| 1 | 7.987 | Full-length cDNA clone CS0DD006YL02 of Neuroblastoma of Homo sapiens (human) | Q86TT1_HUMAN |
| 2 | 5.700 | Ig mu chain C region | A0A087X2C0_HUMAN |
| 3 | 4.557 | Ig mu chain C region | A0A087WYJ9_HUMAN |
| 4 | 3.475 | Alpha-2-macroglobulin | A2MG_HUMAN |
| 5 | 3.453 | Fibrinogen beta chain | FIBB_HUMAN (+1) |
| 6 | 2.982 | Fibrinogen alpha chain | FIBA_HUMAN |
| 7 | 2.638 | Apolipoprotein B (Including Ag(X) antigen) | C0JYY2_HUMAN |
| 8 | 2.468 | Serum albumin | ALBU_HUMAN |
| 9 | 2.223 | APOB protein | Q7Z7Q0_HUMAN |
| 10 | 1.903 | Protein IGHV3-72 | A0A087WW89_HUMAN |
| 11 | 1.737 | C4b-binding protein alpha chain | C4BPA_HUMAN |
| 12 | 1.595 | Fibrinogen gamma chain | FIBG_HUMAN |
| 13 | 1.353 | Haptoglobin (Fragment) | H3BS21_HUMAN |
| 14 | 1.345 | Haptoglobin | H0Y300_HUMAN |
| 15 | 1.140 | IGH@ protein | Q6GMX6_HUMAN |
| 16 | 1.122 | Ig gamma-1 chain C region | A0A087WV47_HUMAN (+1) |
| 17 | 1.113 | Uncharacterized protein | A8K008_HUMAN |
| 18 | 1.055 | Uncharacterized protein | Q6N089_HUMAN |
| 19 | 1.042 | Actin, cytoplasmic 2 | ACTG_HUMAN (+1) |
| 20 | 1.042 | IgG H chain | S6B291_HUMAN |
| 21 | 0.957 | GCT-A10 heavy chain variable region (Fragment) | A0A120HG46_HUMAN |
| 22 | 0.957 | Ig gamma-1 chain C region GN=IGHG1 | A0A087WYC5_HUMAN |
| 23 | 0.942 | cDNA FLJ14473 fis, clone MAMMA1001080, highly similar to Homo sapiens SNC73 protein (SNC73) mRNA | Q96K68_HUMAN |
| 24 | 0.927 | Haptoglobin-related protein | HPTR_HUMAN |
| 25 | 0.915 | Putative uncharacterized protein DKFZp686G11190 | Q6MZQ6_HUMAN |
| 26 | 0.883 | Myosin-reactive immunoglobulin heavy chain variable region (Fragment) | Q9UL90_HUMAN |
| 27 | 0.868 | Putative uncharacterized protein DKFZp686C15213 | Q6MZU6_HUMAN |
| 28 | 0.860 | Ig gamma-3 chain C region | A0A087WXL8_HUMAN |
| 29 | 0.828 | Apolipoprotein E isoform 1 (Fragment) | A0A0S2Z3D5_HUMAN (+1) |
| 30 | 0.785 | Putative uncharacterized protein DKFZp686C11235 GN=DKFZp686C11235 | Q6MZV7_HUMAN |
| 31 | 0.780 | Ig mu heavy chain disease protein | MUCB_HUMAN |
| 32 | 0.772 | IGK@ protein | Q6PIL8_HUMAN |
| 33 | 0.768 | Complement C3 | CO3_HUMAN (+1) |
| 34 | 0.690 | Immunglobulin heavy chain variable region (Fragment) | Q0ZCH9_HUMAN |
| 35 | 0.637 | Beta-globin | D9YZU5_HUMAN (+1) |
| 36 | 0.625 | MS-D4 heavy chain variable region (Fragment) | A0A0X9UWK7_HUMAN |
| 37 | 0.623 | IgG L chain | S6BGD6_HUMAN |
| 38 | 0.620 | Immunoglobulin heavy chain variant (Fragment) | Q9NPP6_HUMAN |
| 39 | 0.612 | Anti-FactorVIII scFv (Fragment) | A2KBC6_HUMAN |
| 40 | 0.607 | Lipoprotein B (Fragment) | S5FLF7_HUMAN |
| 41 | 0.602 | Lambda-chain (AA -20 to 215) | A2NUT2_HUMAN |
| 42 | 0.587 | Mutant hemoglobin alpha 2 globin chain | A0A0K2BMD8_HUMAN (+2) |
| 43 | 0.585 | Protein IGHV3-74 (Fragment) | A0A0B4J1X5_HUMAN |
| 44 | 0.575 | Protein S isoform 1 (Fragment) | A0A0S2Z4K3_HUMAN (+2) |
| 45 | 0.553 | Myosin-reactive immunoglobulin heavy chain variable region (Fragment) | Q9UL88_HUMAN |
| 46 | 0.505 | Apolipoprotein C-III | A3KPE2_HUMAN (+2) |
| 47 | 0.502 | Lectin galactoside-binding soluble 3 binding protein isoform 1 (Fragment) | A0A0S2Z3Y1_HUMAN (+1) |
| 48 | 0.502 | cDNA FLJ53691, highly similar to Serotransferrin | B4E1B2_HUMAN |
| 49 | 0.495 | cDNA, FLJ94213, highly similar to Homo sapiens pregnancy-zone protein (PZP), mRNA | B2R950_HUMAN (+1) |
| 50 | 0.480 | Thrombospondin-1 | TSP1_HUMAN |
| 51 | 0.470 | Protein IGHV5-51 (Fragment) | A0A0C4DH38_HUMAN |
| 52 | 0.458 | Vinculin, isoform CRA_c | A0A024QZN4_HUMAN (+2) |
| 53 | 0.455 | Fibronectin 1, isoform CRA_n | A0A024R462_HUMAN |
| 54 | 0.447 | Apolipoprotein B variant (Fragment) | Q59HB3_HUMAN |
| 55 | 0.437 | Keratin 1 | H6VRF8_HUMAN (+3) |
| 56 | 0.420 | Filamin-A | FLNA_HUMAN |
| 57 | 0.413 | Putative uncharacterized protein DKFZp686L19235 GN=DKFZp686L19235 | Q6MZV6_HUMAN |
| 58 | 0.412 | Ig heavy chain V-III region BUT | HV306_HUMAN |
| 59 | 0.410 | IBM-B2 heavy chain variable region (Fragment) | A0A125QYY9_HUMAN |
| 60 | 0.410 | Alpha-1-antitrypsin | A1AT_HUMAN (+1) |
| 61 | 0.408 | Talin-1 | TLN1_HUMAN |
| 62 | 0.403 | Actinin, alpha 1, isoform CRA_a | A0A024R694_HUMAN (+1) |
| 63 | 0.397 | Apolipoprotein A-I, isoform CRA_a | A0A024R3E3_HUMAN (+1) |
| 64 | 0.392 | Transferrin variant (Fragment) | Q53H26_HUMAN |
| 65 | 0.388 | von Willebrand factor | VWF_HUMAN |

FIG. 10A

| | | | |
|---|---|---|---|
| 66 | 0.387 | Ig gamma-4 chain C region (Fragment) | A0A0G2JPD4_HUMAN (+1) |
| 67 | 0.383 | von Willebrand factor | L8E853_HUMAN |
| 68 | 0.377 | Immunoglobulin light chain (Fragment) | Q0KKI6_HUMAN (+1) |
| 69 | 0.370 | Rheumatoid factor RF-ET9 (Fragment) | A2J1N6_HUMAN |
| 70 | 0.362 | Coagulation factor XIII A chain | F13A_HUMAN |
| 71 | 0.353 | Apolipoprotein C-I, isoform CRA_a | A0A024R0T8_HUMAN (+2) |
| 72 | 0.345 | Rheumatoid factor RF-ET6 (Fragment) | A2J1N5_HUMAN |
| 73 | 0.322 | Complement factor H | CFAH_HUMAN |
| 74 | 0.303 | Keratin, type I cytoskeletal 10 GN=KRT10 | K1C10_HUMAN |
| 75 | 0.302 | Protein APOC4-APOC2 | K7ER74_HUMAN |
| 76 | 0.290 | MS-D3 heavy chain variable region (Fragment) | A0A0X9T7T4_HUMAN |
| 77 | 0.288 | Ig heavy chain V-III region WEA | HV302_HUMAN |
| 78 | 0.287 | Uncharacterized protein | A0A5E4_HUMAN |
| 79 | 0.275 | Keratin, type I cytoskeletal 9 | K1C9_HUMAN |
| 80 | 0.270 | cDNA FLJ75066, highly similar to Homo sapiens complement component 1, r subcomponent (C1R), mRNA | A8K5J8_HUMAN (+1) |
| 81 | 0.265 | Epididymis tissue protein Li 173 | E9KL26_HUMAN (+1) |
| 82 | 0.263 | Myosin, heavy polypeptide 9, non-muscle, isoform CRA_a | A0A024R1N1_HUMAN (+1) |
| 83 | 0.260 | Cryocrystalglobulin CC1 heavy chain variable region (Fragment) | B1N7B6_HUMAN |
| 84 | 0.245 | Putative uncharacterized protein DKFZp686I04196 (Fragment) | Q6N093_HUMAN |
| 85 | 0.235 | Heat shock cognate 71 kDa protein | HSP7C_HUMAN (+1) |
| 86 | 0.233 | Apolipoprotein C-IV | A5YAK2_HUMAN |
| 87 | 0.225 | Hemopexin | HEMO_HUMAN |
| 88 | 0.222 | Epididymis secretory protein Li 52 | V9HWG7_HUMAN (+1) |
| 89 | 0.220 | Actin, alpha skeletal muscle | ACTS_HUMAN (+1) |
| 90 | 0.215 | Keratin, type II cytoskeletal 2 epidermal | K22E_HUMAN |
| 91 | 0.215 | Putative uncharacterized protein DKFZp686M08189 | Q6MZX9_HUMAN |
| 92 | 0.210 | Fermitin family homolog 3 | URP2_HUMAN |
| 93 | 0.208 | Complement C4-B | CO4B_HUMAN |
| 94 | 0.207 | Pyruvate kinase PKM | KPYM_HUMAN (+1) |
| 95 | 0.205 | GCT-A1 heavy chain variable region (Fragment) | A0A125U0V2_HUMAN |
| 96 | 0.202 | Gelsolin | GELS_HUMAN |
| 97 | 0.192 | cDNA FLJ32131 fis, clone PEBLM2000267, highly similar to Tubulin alpha-ubiquitous chain | B3KPS3_HUMAN (+2) |
| 98 | 0.188 | CD5 antigen-like | CD5L_HUMAN |
| 99 | 0.185 | cDNA FLJ56821, highly similar to Inter-alpha-trypsin inhibitor heavy chain H1 | B7Z549_HUMAN (+1) |
| 100 | 0.183 | Immunoglobulin heavy chain variable region (Fragment) | Q0ZCH6_HUMAN |
| 101 | 0.183 | Ig heavy chain V-III region GAL | HV320_HUMAN |
| 102 | 0.178 | Actinin alpha 4 isoform 1 (Fragment) | A0A0S2Z3G9_HUMAN (+1) |
| 103 | 0.178 | Complement component 1, q subcomponent, C chain, isoform CRA_a | A0A024RAA7_HUMAN (+1) |
| 104 | 0.177 | Tubulin alpha-4A chain | TBA4A_HUMAN |
| 105 | 0.170 | cDNA FLJ53487, highly similar to Coagulation factor XIII A chain (EC 2.3.2.13) | B4E2L8_HUMAN |
| 106 | 0.167 | cDNA FLJ35730 fis, clone TESTI2003131, highly similar to ALPHA-1-ANTICHYMOTRYPSIN | B3KS79_HUMAN |
| 107 | 0.165 | Profilin-1 | PROF1_HUMAN |
| 108 | 0.165 | Immunoglobulin J chain | IGJ_HUMAN |
| 109 | 0.165 | Immunoglobulin heavy chain variable region (Fragment) | Q0ZCF6_HUMAN |
| 110 | 0.165 | cDNA FLJ53025, highly similar to Complement C4-B | B7Z1F8_HUMAN |
| 111 | 0.157 | Moesin | MOES_HUMAN (+1) |
| 112 | 0.157 | 78 kDa glucose-regulated protein | GRP78_HUMAN (+1) |
| 113 | 0.157 | Inter-alpha (Globulin) inhibitor H2 | A2RTY6_HUMAN (+3) |
| 114 | 0.157 | IGL@ protein | Q6PIK1_HUMAN |
| 115 | 0.152 | Apolipoprotein M | APOM_HUMAN |
| 116 | 0.152 | cDNA FLJ57038, highly similar to Filamin-A | B4E2F9_HUMAN |
| 117 | 0.150 | Complement component 1, q subcomponent, B chain, isoform CRA_a | A0A024RAB9_HUMAN (+3) |
| 118 | 0.147 | Beta 5-tubulin | Q5SU16_HUMAN (+1) |
| 119 | 0.145 | IgG H chain | S6B2A6_HUMAN |
| 120 | 0.143 | Rheumatoid factor RF-IP12 (Fragment) | A2J1M8_HUMAN |
| 121 | 0.140 | Protein IGHV3-73 | A0A0G2JN55_HUMAN |
| 122 | 0.135 | Lipoprotein, Lp(A) | Q1HP67_HUMAN |
| 123 | 0.132 | Keratin, type I cytoskeletal 16 | K1C16_HUMAN |
| 124 | 0.130 | Heat shock protein HSP 90-alpha | HS90A_HUMAN (+1) |
| 125 | 0.125 | Platelet factor 4 | PLF4_HUMAN |
| 126 | 0.125 | Putative uncharacterized protein DKFZp686C02220 (Fragment) | Q6N091_HUMAN |
| 127 | 0.123 | Apolipoprotein D (Fragment) | C9JF17_HUMAN |
| 128 | 0.120 | Keratin, type I cytoskeletal 14 | K1C14_HUMAN |
| 129 | 0.118 | Tubulin beta-1 chain | TBB1_HUMAN |
| 130 | 0.118 | Inter-alpha (Globulin) inhibitor H4 (Plasma Kallikrein-sensitive glycoprotein) | B2RMS9_HUMAN (+1) |
| 131 | 0.118 | Protein disulfide-isomerase | B3KQT9_HUMAN (+2) |
| 132 | 0.117 | Protein SAA2-SAA4 | A0A096LPE2_HUMAN |
| 133 | 0.112 | CP protein | A5PL27_HUMAN (+3) |
| 134 | 0.110 | Alpha-1B-glycoprotein | A1BG_HUMAN (+1) |
| 135 | 0.110 | Integrin beta-3 | ITB3_HUMAN (+1) |

FIG. 10B

| | | | |
|---|---|---|---|
| 136 | 0.110 | Heparin cofactor 2 | HEP2_HUMAN |
| 137 | 0.108 | Band 3 anion transport protein | B3AT_HUMAN (+3) |
| 138 | 0.107 | Ig heavy chain V-III region CAM | HV307_HUMAN |
| 139 | 0.105 | Apolipoprotein L, 1, isoform CRA_b | A0A024R1G8_HUMAN (+11) |
| 140 | 0.102 | Glycoprotein Ib (Platelet), alpha polypeptide | A0A0C4DGZ8_HUMAN (+2) |
| 141 | 0.102 | Complement C5 | CO5_HUMAN |
| 142 | 0.102 | Endoplasmin | ENPL_HUMAN (+2) |
| 143 | 0.100 | Rheumatoid factor C6 light chain (Fragment) | A0N5G1_HUMAN |
| 144 | 0.098 | Clusterin | CLUS_HUMAN |
| 145 | 0.097 | Adenylyl cyclase-associated protein | D3DPU2_HUMAN |
| 146 | 0.095 | Complement C4-A | A0A0G2JPR0_HUMAN |
| 147 | 0.095 | Complement C1s subcomponent | C1S_HUMAN |
| 148 | 0.093 | cDNA FLJ54184, highly similar to Tropomyosin alpha-4 chain | B4DVY2_HUMAN (+2) |
| 149 | 0.093 | Glyceraldehyde-3-phosphate dehydrogenase | G3P_HUMAN (+1) |
| 150 | 0.092 | Heat shock protein 90kDa alpha (Cytosolic), class B member 1, isoform CRA_a | A0A024RD80_HUMAN (+2) |
| 151 | 0.090 | C4b-binding protein beta chain | C4BPB_HUMAN |
| 152 | 0.090 | Anti-Influenza A hemagglutinin heavy chain variable region (Fragment) | G1FM90_HUMAN |
| 153 | 0.088 | Integrin alpha-IIb | ITA2B_HUMAN |
| 154 | 0.088 | Keratin, type II cytoskeletal 5 | K2C5_HUMAN |
| 155 | 0.087 | Ig heavy chain V-III region GA | HV308_HUMAN |
| 156 | 0.087 | Vitronectin | D9ZGG2_HUMAN (+1) |
| 157 | 0.087 | Plasminogen | PLMN_HUMAN |
| 158 | 0.087 | GCT-A2 heavy chain variable region (Fragment) | A0A125U0V4_HUMAN |
| 159 | 0.085 | Ficolin (Collagen/fibrinogen domain containing) 3 (Hakata antigen), isoform CRA_b | Q6UXM4_HUMAN (+1) |
| 160 | 0.083 | IgGFc-binding protein | A0A087WXI2_HUMAN (+1) |
| 161 | 0.078 | Vitamin D-binding protein | D6RF35_HUMAN |
| 162 | 0.077 | Calreticulin | CALR_HUMAN (+2) |
| 163 | 0.077 | cDNA FLJ53075, highly similar to Kininogen-1 | B4DPP8_HUMAN (+1) |
| 164 | 0.075 | 14-3-3 protein zeta/delta | 1433Z_HUMAN (+1) |
| 165 | 0.075 | Transitional endoplasmic reticulum ATPase | TERA_HUMAN (+1) |
| 166 | 0.073 | Uncharacterized protein (Fragment) | A0A0J9YX35_HUMAN |
| 167 | 0.072 | Platelet glycoprotein V | GPV_HUMAN |
| 168 | 0.072 | cDNA FLJ41552 fis, clone COLON2004478, highly similar to Protein Tro alpha1 H,myeloma | Q6ZW64_HUMAN |
| 169 | 0.070 | Platelet basic protein | CXCL7_HUMAN (+1) |
| 170 | 0.068 | Protein IGHV3-13 (Fragment) | A0A0A0MS11_HUMAN |
| 171 | 0.067 | Complement component 9, isoform CRA_a | A0A024R035_HUMAN (+1) |
| 172 | 0.065 | Proteoglycan 4, isoform CRA_a | A0A024R930_HUMAN (+2) |
| 173 | 0.065 | Protein disulfide-isomerase | A0A024R8S5_HUMAN (+1) |
| 174 | 0.065 | Catalase | CATA_HUMAN |
| 175 | 0.065 | Epididymis luminal protein 180 (Fragment) | B6EDE2_HUMAN |
| 176 | 0.065 | Alpha-1-acid glycoprotein 1 | A1AG1_HUMAN (+1) |
| 177 | 0.063 | Heat shock 70 kDa protein 1B | A0A0G2JIW1_HUMAN (+3) |
| 178 | 0.063 | Prenylcysteine oxidase 1 | PCYOX_HUMAN |
| 179 | 0.063 | Integrin-linked protein kinase | A0A0A0MTH3_HUMAN (+2) |
| 180 | 0.063 | Carboxypeptidase N subunit 2 | CPN2_HUMAN |
| 181 | 0.063 | Anti-streptococcal/anti-myosin immunoglobulin kappa light chain variable region (Fragment) | Q96SA9_HUMAN |
| 182 | 0.063 | GCT-A5 light chain variable region (Fragment) | A0A0X9UWL5_HUMAN |
| 183 | 0.062 | Zyxin GN=ZYX | ZYX_HUMAN |
| 184 | 0.062 | V2-17 protein (Fragment) | Q5NV90_HUMAN |
| 185 | 0.062 | Myosin-reactive immunoglobulin heavy chain variable region (Fragment) | Q9UL89_HUMAN |
| 186 | 0.060 | cDNA FLJ54622, highly similar to Prothrombin (EC 3.4.21.5) | B4DDT3_HUMAN (+1) |
| 187 | 0.060 | Multimerin-1 | MMRN1_HUMAN |
| 188 | 0.058 | Tropomyosin 3 isoform 1 (Fragment) | A0A0S2Z4G4_HUMAN (+1) |
| 189 | 0.058 | Ig gamma-1 chain C region | A0A087X1C7_HUMAN |
| 190 | 0.057 | Alpha-2-antiplasmin | A2AP_HUMAN |
| 191 | 0.057 | Ig heavy chain variable region (Fragment) | A0A068LRW6_HUMAN (+2) |
| 192 | 0.057 | Enolase 1, (Alpha), isoform CRA_a | A0A024R4F1_HUMAN (+1) |
| 193 | 0.057 | Apolipoprotein A-IV | APOA4_HUMAN |
| 194 | 0.057 | MS-D1 light chain variable region (Fragment) | A0A0X9TD47_HUMAN |
| 195 | 0.055 | Uncharacterized protein | B4E1Z4_HUMAN |
| 196 | 0.055 | Calpain 1, (Mu/I) large subunit, isoform CRA_a | A0A024R5B0_HUMAN (+2) |
| 197 | 0.055 | GCT-A8 heavy chain variable region (Fragment) | A0A0X9V9C4_HUMAN |
| 198 | 0.055 | Serpin peptidase inhibitor, clade C (Antithrombin), member 1, isoform CRA_a | A0A024R944_HUMAN (+1) |
| 199 | 0.052 | Protein AMBP | AMBP_HUMAN |
| 200 | 0.050 | Fructose-bisphosphate aldolase A | ALDOA_HUMAN (+2) |

FIG. 10C

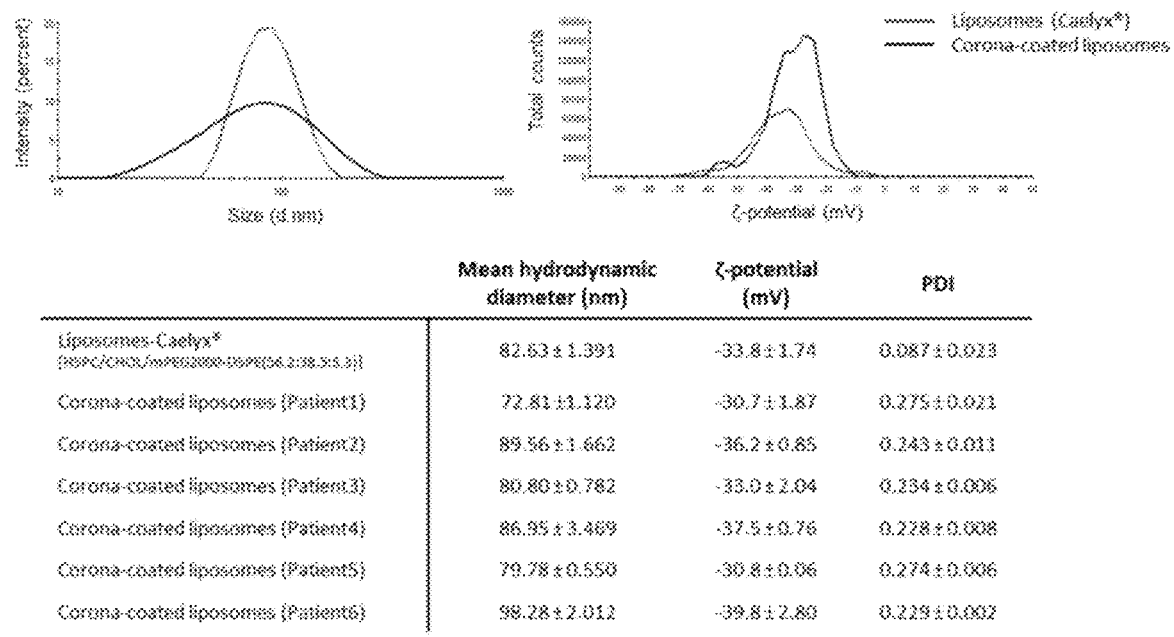
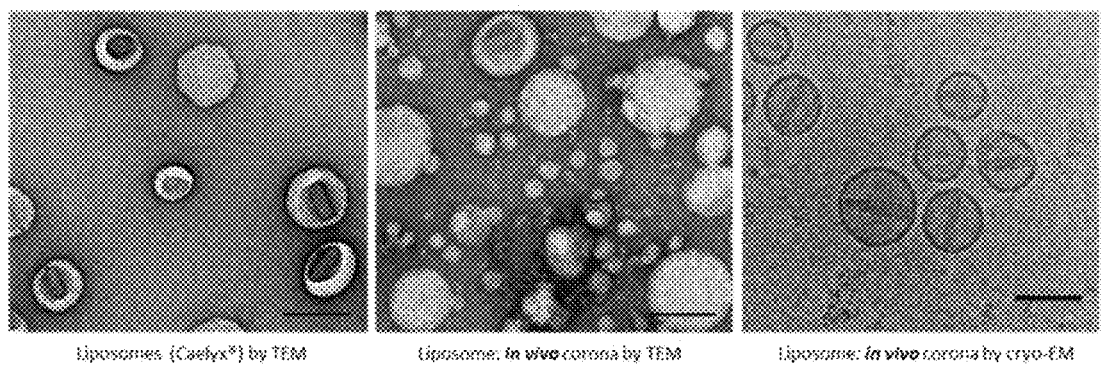
FIG. 12

DETECTION OF CANCER BIOMARKERS USING NANOPARTICLES

FIELD OF THE INVENTION

The present invention relates to methods for identifying and detecting potential disease specific biomarkers from biofluids. In particular, the methods involve administration of nanoparticles to a subject in a diseased state or incubation of nanoparticles in a biofluid sample taken from a subject in a diseased state and subsequent analysis of the biomolecule corona formed on said nanoparticles. In addition, the present invention also relates to methods that provide a means to distinguish between healthy and diseased states in a subject, such as for example the early detection of a tumor in a human subject or the presence or monitoring of the growth and/or response to treatment of a tumor in a human subject.

BACKGROUND OF THE INVENTION

A biomarker, or biological marker, generally refers to a qualitative and/or quantitative measurable indicator of some biological state or condition. Biomarkers are typically molecules, biological species or biological events that can be used for the detection, diagnosis, prognosis and prediction of therapeutic response of diseases. Most biomarker research has been focused on measuring a concentration change in a known/suspected biomarker in a biological sample associated with a disease. Such biomarkers can exist at extremely low concentrations, for example in early stage cancer, and accurate determination of such low concentration biomarkers has remained a significant challenge.

Research into nanoparticle-based technologies for biomarker detection has been carried out but so far has failed to provide suitable methods to accurately identify/discover and detect biomarkers. One particular problem is that currently available laboratory tests detect only a minute fraction of potential biomarkers, due to their extremely low concentration in biofluids. In addition to the 'swamping' effect, caused by "non-specific" high abundant molecules, this casuses significant difficulties. Indded, the issue of "signal-to-noise" exceeds the current capability of proteomic analysis and therefore limits the diagnostic information that can be obtained.

Furthermore, such methods are mainly used to detect already known disease-specific molecules. For example, nanoparticle-based immunoassays, such as sandwich-type assays have been developed, where nanoparticles are used to fluorophore-label the secondary antibody to a known disease-specific molecule. The presence of a target biomarker generates a fluorescent signal that is detected using microscopy or a fluorescence spectrophotometer. NanoDLSay™ is a particular nanoparticle-based immunoassay that detects specific known biomarkers by measuring the size change of gold nanoparticle probes upon binding with target molecules. Gold nanoparticles conjugated to specific antibodies are mixed in vitro with biofluids. The binding of proteins with the gold nanoparticle immunoprobes can lead to nanoparticle cluster or aggregate formation. The average particle size increase of the assay solution is measured and correlated to the target protein concentration.

Nanoparticle-based immunoassays are inherently limited by the detection of a single molecule-biomarker. In order to increase the sensitivity and specificity of detection, biomarkers can, for example, be regarded as a panel of up- and down-regulated proteins, which differ in diseased and normal state. 'Multiplexing' is a difficult and highly expensive challenge with such technologies.

In vitro nanoparticle-based scavenger technologies such as Nanotrap® particle technology uses hydrogel nanoparticles with a porous outer shell that blocks the entry of high molecular weight proteins and an internal core which contains chemical affinity baits for interaction with low molecular weight proteins, after the introduction of nanoparticles into biological fluids. The limitation of this approach is that some of the high molecular weight proteins removed are known to act as 'carriers' for other proteins, possibly with biomarker potential.

Surprisingly, the inventors have found that analyzing the biomolecule corona formed on nanoparticles after following methods involving administration of nanoparticles to a subject in a diseased state or incubation of nanoparticles in a biofluid sample taken from a subject in a diseased state results in interaction of the nanoparticles with many more different types of biomolecules in comparison with analysis of biomolecules directly in biofluid samples. In one embodiment, the novel methods take advantage of the interaction of nanoparticles with biomolecules as a way to more comprehensively analyse the circulatory proteome and facilitate the detection of previously unknown disease-specific biomolecules.

In addition, inventors have also surprisingly found that particular methods of the invention can be employed to distinguish between healthy and disease states in a subject, for example the detection of the presence of a tumor or monitoring the growth and/or response to treatment of a tumor.

SUMMARY OF THE INVENTION

In one aspect, the present invention relates to a method of identifying a biomarker from a biofluid, wherein the method comprises:
  a. administering a plurality of nanoparticles to a subject in a diseased state to allow a biomolecule corona to form on the surface of said nanoparticles or incubating a plurality of nanoparticles in a biofluid sample taken from a subject in a diseased state to allow a biomolecule corona to form on the surface of said nanoparticles;
  b. isolating the nanoparticles and surface-bound biomolecule corona; and
  c. analyzing the biomolecule corona to identify the said biomarker.

The methods result in an interaction between the nanoparticles and a greater number of different types of proteins than can be detected by direct analysis of biofluids taken from a subject in a diseased state. It is to be understood that the method involves identification of a biomarker that provides a measurable indicator of some biological state or condition. This includes, but is not limited to, the discovery of unique disease-specific biomolecules (those biomolecules that are only present in a diseased state) but also includes detection of changes in biomolecule(s) that are present in both healthy and diseased states, for example upregulation or down regulation of biomolecules in a diseased state when compared to the healthy state. It will be understood that in order to identify a potential disease-specific biomarker, comparison against a suitable non-diseased control reference can be required. In one particular embodiment, the methods involve identifying panels of biomarkers (multiplexing), which can lead to increased sensitivity and specificity of detection. In a further particular embodiment, the methods facilitate the detection of previously unknown unique disease-specific biomolecules. In yet a further particular embodiment, the methods allow identification or detection of a biomarker without the need for invasive tissue sampling, e.g. a biopsy.

The methods are applicable to a wide range of nanoparticles and allow the benefit of removal of unbound and highly abundant biomolecules to allow identification of low abundant biomarkers that would otherwise be undetected. In addition to identification of potential biomarkers, the methods can also be employed to monitor changes in biomarkers, for example in response to therapy and/or to assist in diagnosis.

In another aspect, the present invention relates to a method of detecting a diseased state in a subject, wherein the method comprises:
a. administering a plurality of nanoparticles to a subject to allow a biomolecule corona to form on the surface of the nanoparticles;
b. isolating the nanoparticles and surface-bound biomolecule corona; and
c. determining the total biomolecule content of the biomolecule corona, which is determinative of the presence of disease in said subject.

Surprisingly, inventors have found that particular methods can be employed to distinguish between healthy and diseased states in a subject. Such methods can, for example, be useful in the early detection of a diseased state such as the presence of a tumor in a human subject.

The methods disclosed herein are applicable to any disease state in which identification and/or monitoring of biomarkers would be beneficial. Furthermore, particular methods of the invention, which an be employed to distinguish between healthy and diseased states in a subject, are applicable to a wide range of diseases, including but not limited to, cancer and neurodegenerative diseases.

BRIEF DESCRIPTION OF DRAWINGS

FIG. 4a provides a breakdown of the host proteins identified following in vivo administration;

FIG. 4b provides after in vitro incubation in the lung adenocarcinoma model, ranked by fold change in amount of that protein detected in the protein corona from healthy and diseased mice (proteins with greater than 5 fold change shown);

FIG. 5a provides a breakdown of the proteins identified following in vivo administration;

FIG. 5b provides after in vitro incubation in the melanoma model ranked by fold change in amount of that protein detected in samples from healthy and diseased mice (proteins with greater than 5 fold change shown);

FIG. 9 provides a breakdown of the top 10 proteins identified in the nanoparticle protein corona based on Relative Protein Abundance (represents the percentage of each protein relative to the total amount of protein purified from the protein corona of the nanoparticles) following in vivo administration to 6 patients. FIG. 9 also provides a list of the top 10 most abundant proteins found in plasma taken from one of the patients (Patient 1). The data demonstrates that the methods of the invention are able to extract out different types of proteins from the patients that are not readily detectable in plasma;

FIG. 10 provides a breakdown of the top 200 proteins identified in the nanoparticle protein corona based on the RPA % following in vivo administration to 6 patients (RPA % data is based on the mean of the six patients). The data further demonstrates that the methods of the invention are able to extract out different types of proteins from the patients that are not readily detectable in plasma;

FIG. 12 shows data before and after dosing of Dynamic light scattering (DLS), ζ-potential measurements and negative stain transmission electron microscopy (TEM) showing physicochemical characteristics of the PEGylated doxorubicin-encapsulated liposomes (Caelyx®);

METHOD FOR IDENTIFYING NEW BIOMARKERS

Figure 1:
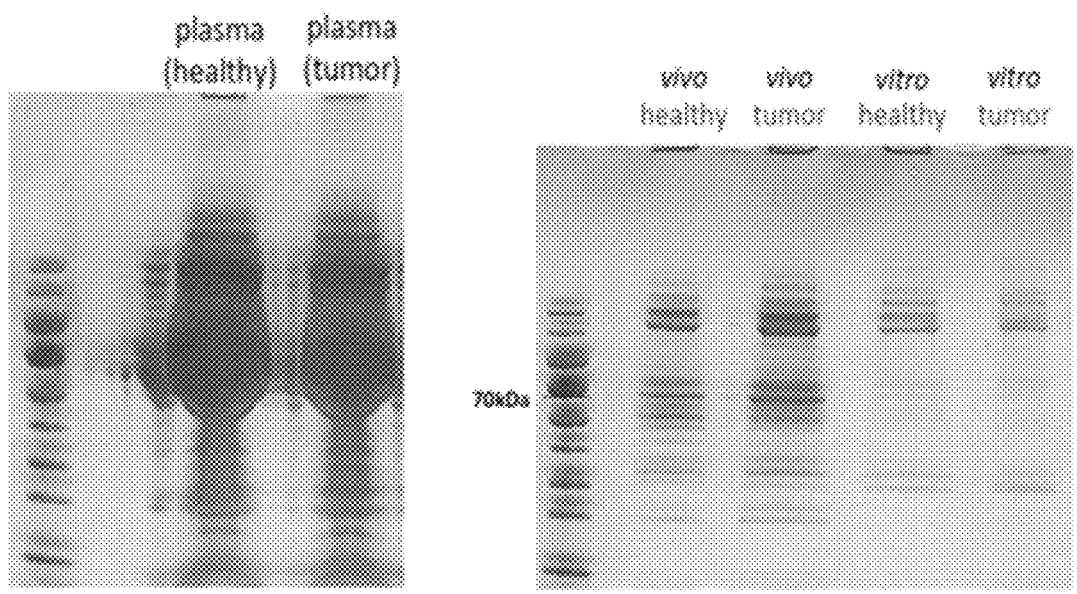
FIG. 1 shows the SDS-Page gel for protein recovered directly from plasma compared with the analysis conducted following either in vivo administration of nanoparticles in mice or after in vitro incubation with plasma taken from mice. Data is presented for healthy or tumor bearing mice (i.e. lung adenocarcinoma model)

Methods provided by the present invention include those described generally above, and are further illustrated by all of the particular method steps disclosed herein.

The present invention relates to a method of identifying a biomarker from a biofluid, wherein the method comprises:
a. administering a plurality of nanoparticles to a subject in a diseased state to allow a biomolecule corona to form on the surface of said nanoparticles or incubating a plurality of nanoparticles in a biofluid sample taken from a subject in a diseased state to allow a biomolecule corona to form on the surface of said nanoparticles;
b. isolating the nanoparticles and surface-bound biomolecule corona; and
c. analyzing the biomolecule corona to identify the said biomarker.

The present invention relates to a method of identifying a biomarker from a biofluid. In a particular embodiment of the present invention, the biomarker comprises at least one biomolecule (for example, a protein, peptide, fatty acid, lipid, amino acid, sugar, amide or nucleic acid) and the biofluid is selected from plasma, urine, saliva, lacrimal, cerebrospinal and occular fluids. In a particular embodiment, the biofluid is plasma and the biomarker is at least one protein.

The present invention involves the use of a plurality of nanoparticles. The methods are applicable to any types of nanoparticles capable of attracting a biomolecule corona. In a particular embodiment, the nanoparticles are selected from liposomes, gold nanoparticles, polymeric nanoparticles, carbon nanotubes and graphene oxide nanoparticles.

Conveniently, the nanoparticles are liposomes. Liposomes are generally spherical vesicles comprising at least one lipid bilayer. Liposomes are often composed of phospholipids. In a particular embodiment, the liposomes are composed of phospholipid molecules and functionalised amphiphilic molecules (eg. PEGylated DSPE) that are able to self-assemble into unilamellar vesicles. Conveniently, the liposomes are able to encapsulate drug molecules in their inner aqueous phase.

The corona formed on the nanoparticles is a biomolecule corona. The term "biomolecule" in this context includes, but is not limited to, proteins, peptides, fatty acids, lipids, amino acids, amides, sugars and nucleic acids (such as for example different types of DNA or RNA). Conveniently, the biomolecule corona comprises a protein corona.

Step (a) of the method involves administering a plurality of nanoparticles to a subject in a diseased state to allow a biomolecule corona to form on the surface of said nanoparticles or incubating a plurality of nanoparticles in a biofluid sample taken from a subject in a diseased state to allow a biomolecule corona to form on the surface of said nanoparticles. Where the plurality of nanoparticles are administered to a subject in a diseased state to allow a biomolecule corona to form on the surface of said nanoparticles, administration can be by any route that allows the biomolecule corona to form. Suitable routes of administration include but are not limited to intravenous, oral, intracerebral (including spinal), intraperitoneal and intra-occular. Conveniently, the route of administration is by intravenous injection. The biomolecule corona typically forms within less than 10 minutes from administration.

In the case where the plurality of nanoparticles are incubated in a biofluid sample taken from a subject in a diseased state, such incubation can be carried out in-vitro. Conveniently, this involves incubating at 37° C. the nanoparticles with plasma taken from the subject in the diseased state for a minimum period of 10 minutes, although it is possible that biomolecule corona can form immediately upon incubation. Conveniently, the mixture can be subject to agitation, for example by way of an orbital shaker set at approximately 250 rpm to mimic in vivo conditions.

Once the biomolecule corona has formed on said nanoparticles, said particles are isolated. Any isolation technique that is capable of preserving the surface-bound biomolecule corona is suitable. Conveniently, the nanoparticles with surface-bound biomolecule corona are isolated from the biofluid and purified to remove unbound and highly abundant biomolecules (for example albumin and/or immunoglobulins, which can constitute 90% of the plasma proteome) to allow identification of lower abundant biomarkers. The method therefore allows minimization of any masking caused by the highly abundant proteins. Conveniently, the isolation is achieved by a method comprising size exclusion chromatography followed by ultrafiltration. The method offers particular benefits over centrifugation methodologies that favour interaction with proteins. In a particular embodiment, the method allows identification of low molecular weight protein biomarkers. Conveniently, the method allows identification of protein biomarkers with molecular weight of less than 80 kDa. More conveniently, the method allows identification of protein biomarkers with molecular weight of less than 40 kDa or less than 20 kDa. In a particular embodiment of the invention, the beneficial sensitivity and high level of precision provided by the method allows the identification of intracellular protein disease related biomarkers that are present in low abundance and would otherwise be very difficult to identify.

Analysis of the biomolecule corona in order to identify biomarkers can be carried out using any suitable technique capable of detecting said biomarkers. In a particular embodiment of the invention, the biomolecule corona is analysed by gel electrophoresis, mass spectrometry, an immunoassay, UV-Vis. absorption, fluorescence spectroscopy, chromatography or NMR methodology. Conveniently, the biomolecule corona is analysed by mass spectrometry, which can allow qualitative and/or quantitative analysis of the biomolecule corona present on the nanoparticles. In a particular embodiment, certain methods may allow identification of unique biomolecules without the need for highly specialized and ultra-sensitive analytical mass spectrometry instrumentation such as an UltiMate® 3000 Rapid Separation LC (RSLC, Dionex Corporation, Sunnyvale, Calif.) coupled to a LTQ Velos Pro (Thermo Fisher Scientific, Waltham, Mass.) mass spectrometer. In one aspect of this embodiment, analysis of the biomolecule corona is carried out after administering a plurality of nanoparticles to a subject in a diseased state to allow a biomolecule corona to form on the surface of said nanoparticles and isolating the nanoparticles and surface-bound biomolecule corona. When compared to other methods, such methods can yield high levels of unique low abundant biomolecules and allow identification of such unique biomolecules without the need for highly specialized and ultra-sensitive analytical mass spectrometry instrumentation such as an UltiMate® 3000 Rapid Separation LC (RSLC, Dionex Corporation, Sunnyvale, Calif.) coupled to a LTQ Velos Pro (Thermo Fisher Scientific, Waltham, Mass.) mass spectrometer.

In addition to the identification of a single biomarker, the methods also provide the ability to identify panels of biomarkers (multiplexing). This approach can lead to increased sensitivity and specificity of detection.

In addition to the identification of new biomarkers, the methods also provide the ability to monitor changes in biomarkers for example in response to therapy. In one particular embodiment the therapy administered to the subject prior to testing is a drug molecule, such as for example, an anti-cancer compound. Suitable anti-cancer compounds include, but are not limited to, compounds with activity in cancers such as lung cancer, melanoma or ovarian cancer. Conveniently, the anti-cancer compound is doxorubicin.

In a particular embodiment, the invention relates to a method of identifying a biomarker from a biofluid, wherein the method comprises:
 a. isolating a plurality of nanoparticles with surface-bound biomolecule corona from a biofluid sample taken from a subject in a diseased state; and
 b. analyzing the biomolecule corona to identify the said biomarker.

Method of Detecting a Diseased State in a Subject

The present invention also relates to a method of detecting a diseased state in a subject, wherein the method comprises:
 a. administering a plurality of nanoparticles to a subject to allow a biomolecule corona to form on the surface of the nanoparticles;
 b. isolating the nanoparticles and surface-bound biomolecule corona; and
 c. determining the total biomolecule content of the biomolecule corona, which is determinative of the presence of disease in said subject.

Surprisingly, inventors have found that the analysis of the total biomolecule content of the biomolecule corona isolated after administering a plurality of nanoparticles to a subject to allow a biomolecule corona to form on the surface of the nanoparticles is indicative of the presence of disease in said subject. In a particular embodiment, the biomolecule is a protein.

The total biomolecule content of the biomolecule corona can be determined by any method capable of quantifying the level of said biomolecules in the surface-bound corona. In one embodiment, the biomeolecule method involves determining the total protein content and this is suitably determined by a bicinchoninic acid assay (BCA assay). In one particular embodiment, the subject is a human patient and the total protein content is at least 700, 800, 900, 1000, 1250, 1500, 1800, 2000, 25000 or 3000 Pb when measured using a BCA assay. In yet a further aspect of this embodiment, the disease state is cancer, such as for example ovarian cancer, lung cancer or melenoma.

Figure 11:
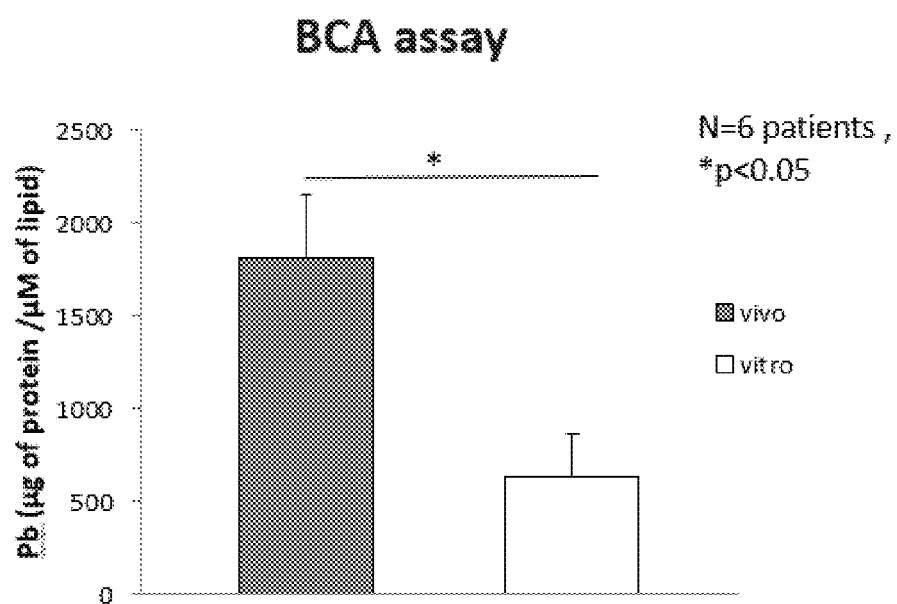
FIG. 11 provides the results for the BCA assay for the human patient study. The level of total amount of protein detected in the protein corona from patients following in vivo administration is significantly greater than after in vitro incubation of the nanoparticles in plasma taken from such patients.

Surprisingly, inventors have also found that the total protein content determined by the inventive method is greater than if determined by incubating the plurality of nanoparticles in-vitro with a biofluid taken from the subject. FIG. 11 shows data to illustrate this surprising discovery. In a particular embodiment, the total protein content determined is at least between 1.2 and 5 fold higher than if determined by incubating the plurality of nanoparticles in-vitro with a biofluid isolated from the subject. Conveniently, total protein content determined is at least 1.5, 1.8, 2, 3, 4 or 5 fold higher than if determined by incubating the plurality of nanoparticles in-vitro with a biofluid isolated from the subject. Conveniently, the subject in this embodiment is a human.

Conveniently, the route of administration of the nanoparticles is by intravenous injection. The biomolecule corona typically forms within less than a few minutes from administration.

Any isolation technique that is capable of preserving the surface-bound biomolecule corona is suitable. Conveniently, the nanoparticles with surface-bound biomolecule corona are isolated from the biofluid and purified to remove unbound and highly abundant biomolecules (for example albumin) to allow identification of lower abundant biomarkers. The method therefore allows minimization of any masking caused by the highly abundant proteins. Conveniently, the isolation is achieved by a method comprising size exclusion chromatography followed by ultrafiltration.

In addition to a determination of the total biomolecule content of the biomolecule corona, analysis of the biomolecule corona can also reveal qualitative and quantitative information regarding specific potential biomarkers. Such analysis can be carried out using any suitable techniques of capable of detecting said biomarkers. In a particular embodiment of the invention, the biomolecule corona is analysed by mass spectrometry, an immunoassay, UV-Vis. absorption, fluorescence spectroscopy, chromatography or NMR methodology. Conveniently, the biomolecule corona is analysed by mass spectrometry, which can allow qualitative and quantitative analysis of the biomolecule corona present on the nanoparticles. In a particular embodiment, the methods allow identification of unique biomolecules without the need for highly specialized and ultra-sensitive analytical mass spectrometry instrumentation such as using an UltiMate® 3000 Rapid Separation LC (RSLC, Dionex Corporation, Sunnyvale, Calif.) coupled to a LTQ Velos Pro (Thermo Fisher Scientific, Waltham, Mass.) mass spectrometer.

A further aspect of the invention includes novel biomarkers that are linked with particular diseases, such as ovarian cancer, lung cancer or melanoma and could facilitate personalized healthcare and patient selection and stratification strategies for therapy. Examples of such biomarkers are further described in the experimental examples below.

EXAMPLES

Further examples of the invention are described hereinbelow, by way of example only, with reference to the accompanying figures.

Example 1. Xenograft Mice Models

Six to eight week old male nude SCID beige mice were purchased from Charles River (UK). Five to six week old female C57BL/6 mice were purchased from Charles River (UK). Animal procedures were performed in compliance with the UK Home Office Code of Practice for the Housing and Care of Animals used in Scientific Procedures. Mice were housed in groups of five with free access to water and kept at temperature of 19-22° C. and relative humidity of 45-65%. Before performing the procedures, animals where acclimatized to the environment for at least 7 days.

Lung Adenocarcinoma Model:

Six to eight weeks old male nude SCID beige mice were intravenously injected (via tail vein) with a549-luc cells (5E6 cell/200 ul of PBS).

Melanoma Model:

Five to six week old female C57BL/6 mice were subcutaneously injected (to the left leg) with $0.5 \times 10^6$ of B 16F10-luc melanoma cells in a volume of 50 µl of PBS.

Preparation of Liposome Nanoparticles

Materials

Hydrogenated soy phosphatidylcholine (HSPC), 1,2-distearoyl-sn-glycero-3-phosphoethanolamine-N-[methoxy (polyethylene glycol)-2000 (DSPE-PEG2000) were purchased from Avanti Polar Lipids (USA), while cholesterol was purchased from Sigma (UK).

Preparation Methods

Liposomes with a composition of (HSPC:CHOL:DSPE-PEG2000 (56.3:38.2:5.5) were prepared by thin lipid film hydration method followed by extrusion. Briefly, lipids were dissolved in chloroform:methanol mixture (4:1) in a total volume of 2 ml, using a 25 ml round bottom flask. Organic solvents were then evaporated using a rotary evaporator (Buchi, Switzerland) at 40° C., at 150 rotations/min, 1 h under vacuum. Lipid films were hydrated with ammonium sulphate 250 mM (pH 8.5) at 60° C. to produce large multilammelar liposomes. Small unilamellar liposomes were then produced by extrusion though 800 nm and 200 nm polycarbonate filters (Whatman, VWR, UK) 10 times each and then 15 times through 100 nm and 80 nm extrusion filters (Whatman, VWR, UK) using a mini-Extruder (Avanti Polar Lipids, Alabaster, Ala.).

Protein Corona Formation after In Vivo Administration of Nanoparticles in Mice

Mice were anesthetized by inhalation of isoflurane and liposomes were administered intravenously via the lateral tail vein, at a lipid dose of 0.125 mM/g body weight, used for preclinical studies. 10 minutes post-injection, blood was recovered by cardiac puncture using K2EDTA coated blood collection tubes. Plasma was prepared by inverting the collection tubes 10 times to ensure mixing of blood with EDTA and subsequent centrifugation for 12 minutes at 1300 RCF at 4° C. Supernatant was collected into Protein LoBind Eppendorf Tubes. The plasma samples obtained from three mice were pooled together.

Protein corona formation after in vitro incubation with plasma taken from mice The in vitro formed corona was allowed to form using a liposome concentration of 2.25 mM, which is equivalent to the typical concentration of liposomes found in plasma after in vivo administration to mice as described above. For all in vitro protein binding studies, 2.25 mM of liposomes (180 µl of 12.5 mM) were incubated with 820 µl of mouse plasma for 10 min at 37° C. in orbital shaker at 250 rpm setting to mimic in vivo conditions.

Separation of Corona-Coated Nanoparticles from Unbound and Weakly Bound Proteins Nanoparticles recovered from the in vivo or in vitro experiments described above were separated from excess plasma proteins by size exclusion chromatography followed by membrane ultrafiltration Immediately after in vitro or in vivo incubations, 1 ml of plasma samples was loaded onto a Sepharose CL-4B (SIGMA-ALDRICH) column (15×1.5 cm) equilibrated with HBS. Stewart assay in each chromatographic fraction (1 ml) revealed that nanoparticles were eluted in fractions 4, 5 and 6. Fractions containing nanoparticles were then pooled together and concentrated to 500 µl by centrifugation using Vivaspin 6 column (10000 MWCO, Sartorious, Fisher Scientific) at 9000 rpm. Vivaspin 500 centrifugal concentrator (1 000 000 MWCO, Sartorious, Fisher Scientific) was then used at 9000 rpm, to further concentrate the samples to 100 µl and to ensure separation of protein-coated nanoparticles from the remaining large unbound proteins. Nanoparticles were then washed 3 times with 100 µl HBS to remove weekly bound proteins SDS-PAGE Electrophoresis Samples of protein corona-coated nanoparticles were mixed with 20 ul of Tris-Glycine SDS buffer, with 4 ul of NuPAGE REDUCING and with water for a final volume of 40 µl and boiled for 5 minutes at 90° C. Samples were then loaded in 4-20% NOVEX Tris-Glycine Protein Gel (ThermoFisher Scientific). The gel was run for 25-40 minutes at 225V, until the proteins neared the end of the gel, in 10 times diluted Novex® Tris-Glycine SDS Running Buffer (ThermoFisher Scientific). Staining was performed with Imperial Gel Staining reagent (Sigma Life Science) for an hour followed by washing in distilled water for 2 days.

FIG. 1 shows the SDS-Page gel for protein recovered directly from plasma (healthy and tumor, i.e. lung adenocarcinoma model) where a large signal is present as a result of highly abundant proteins such as albumin. In contrast, the SDS-Page gel for analysis conducted following either in vivo administration of nanoparticles in mice or after in vitro incubation with plasma taken from mice, does not exhibit the masking problem and the data reveals the presence of a number of lower abundant proteins.

Figure 2:
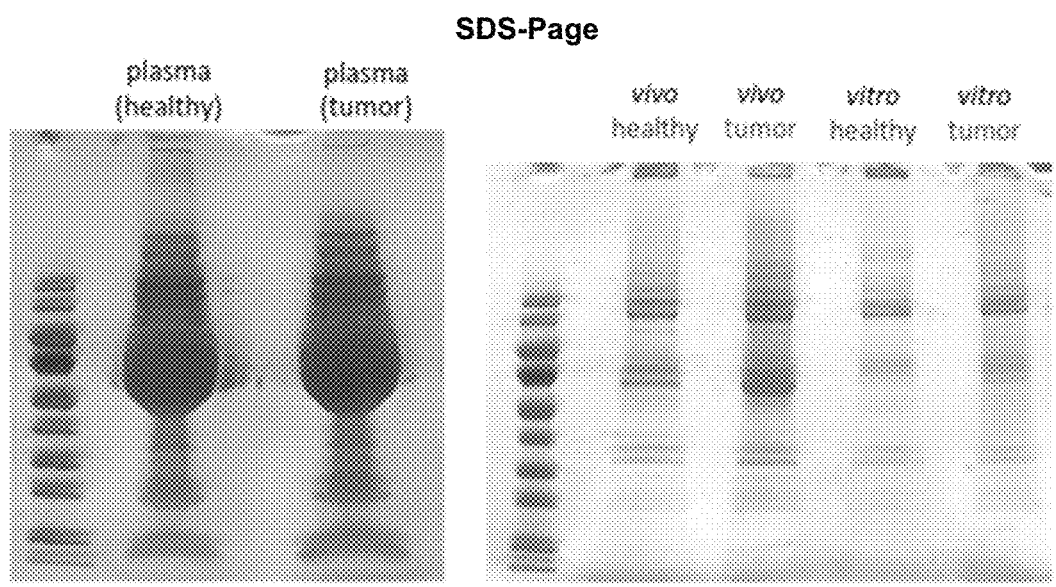
FIG. 2 shows the SDS-Page gel for protein recovered directly from plasma compared with the analysis conducted following either in vivo administration of nanoparticles in mice or after in vitro incubation with plasma taken from mice. Data is presented for healthy or tumor bearing mice (i.e. melanoma model)

Similar differences are also evident for the melanoma model (FIG. 2).

Mass Spectrometry

Bands of interest were excised from the SDS-Page gel and dehydrated using acetonitrile followed by vacuum centrifugation. Dried gel pieces were reduced with 10 mM dithiothreitol and alkylated with 55 mM iodoacetamide. Gel pieces were then washed alternately with 25 mM ammonium bicarbonate followed by acetonitrile. This was repeated, and the gel pieces dried by vacuum centrifugation. Samples were digested with trypsin overnight at 37° C.

Digested samples were analysed by LC-MS/MS using an UltiMate 3000 Rapid Separation LC (RSLC, Dionex Corporation, Sunnyvale, Calif.) coupled to Orbitrap Velos Pro (Thermo Fisher Scientific, Waltham, Mass.) mass spectrometer. Peptide mixtures were separated using a gradient from 92% A (0.1% FA in water) and 8% B (0.1% FA in acetonitrile) to 33% B, in 44 min at 300 nL min$^{-1}$, using a 250 mm×75 µm i.d. 1.7 µM BEH C18, analytical column (Waters). Peptides were selected for fragmentation automatically by data dependant analysis. Data produced were searched using Mascot (Matrix Science UK), against the uniprot_concat2014_201410. fasta database. Data presented in FIG. 3 was validated using Scaffold (Proteome Software, Portland, Oreg.) and data presented in FIGS. 4a, 4b, 5a and 5b were validated using Progenesis QI for Proteomics.

The Scaffold software (version Scaffold_4.4.5, Proteome Software Inc., Portland, Oreg.) was used to validate MS/MS based peptide and protein identifications and for relative quantification based on spectral counting. Peptide identifications were accepted if they could be established at greater than 50.0% probability by the Peptide Prophet algorithm with Scaffold delta-mass correction. Protein identifications were accepted if they could be established at greater than 99.0% probability and contained at least 2 identified peptides. Protein probabilities were assigned by the Protein Prophet algorithm. Proteins that contained similar peptides and could not be differentiated based on MS/MS analysis alone were grouped to satisfy the principles of parsimony.

Figure 3:
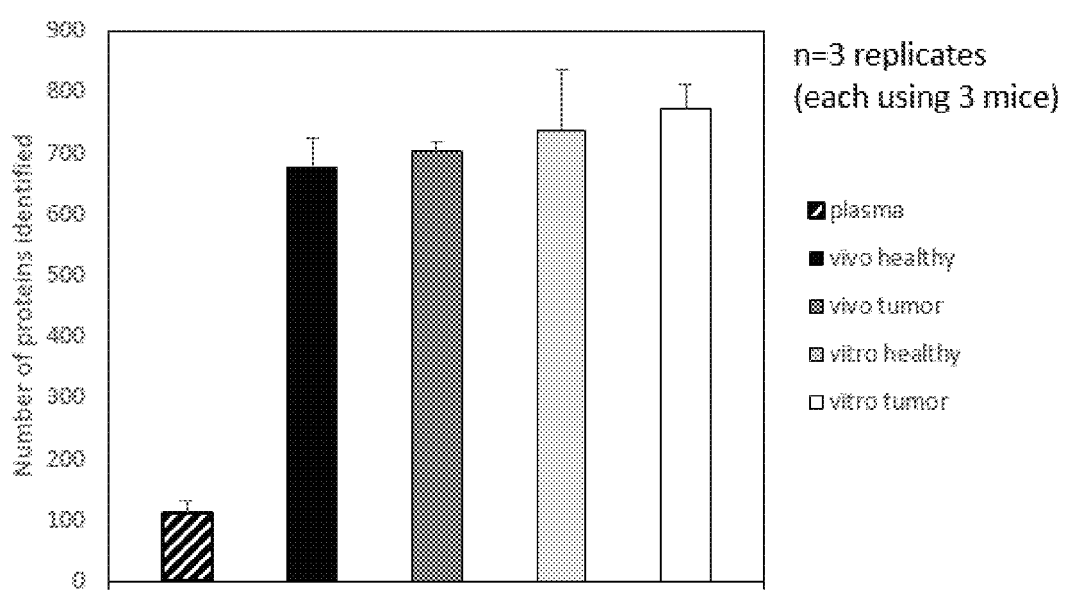
FIG. 3 shows the number of proteins identified following in vivo administration of nanoparticles in mice or after in vitro incubation when compared with plasma. The data demonstrates that a significantly higher number of proteins were identified when compared to plasma. Data generated using lung adenocarcinoma model.

The improved ability to identify a greater number of proteins is also demonstrated in FIG. 3 (lung adenocarcinoma model), which shows the number of proteins identified following in vivo administration of nanoparticles in mice or after in vitro incubation with mouse plasma when compared with plasma analysis (data presented is the result of analysis conducted with Scaffold software as described above). The data demonstrates that a significantly higher number of corona proteins identified when compared to plasma analysis.

FIG. 4a provides a breakdown of the host proteins identified following in vivo administration and FIG. 4b provides after in vitro incubation in the lung adenocarcinoma model, ranked by fold change in amount of that protein detected in the protein corona from healthy and diseased mice (proteins with greater than 5 fold change shown). The data demonstrates that the methods are able to identify changes in proteins between tumor and healthy groups. Particular human tumour specific proteins were also identified in the nanoparticle protein corona of diseased mice in this lung adenocarcinoma model that involves the use of the human derivved a549-luc cancer cell line. This demonstrates the ability of the method to detect proteins secreted by the human tumour. Data presented is the result of analysis conducted with Progenesis QI for Proteomics as described above.

FIG. 5a provides a breakdown of the proteins identified following in vivo administration and FIG. 5b provides after in vitro incubation in the melanoma model ranked by fold change in amount of that protein detected in samples from healthy and diseased mice. The data demonstrates that the methods are able to identify changes in proteins between tumor and healthy groups. Data presented is the result of analysis conducted with Progenesis QI for Proteomics as described above.

The accession numbers of the proteins indicated in FIGS. 4a, 4b, 5a and 5b were assigned using uniprot_concat2014_201410.fasta database.

Figure 14:
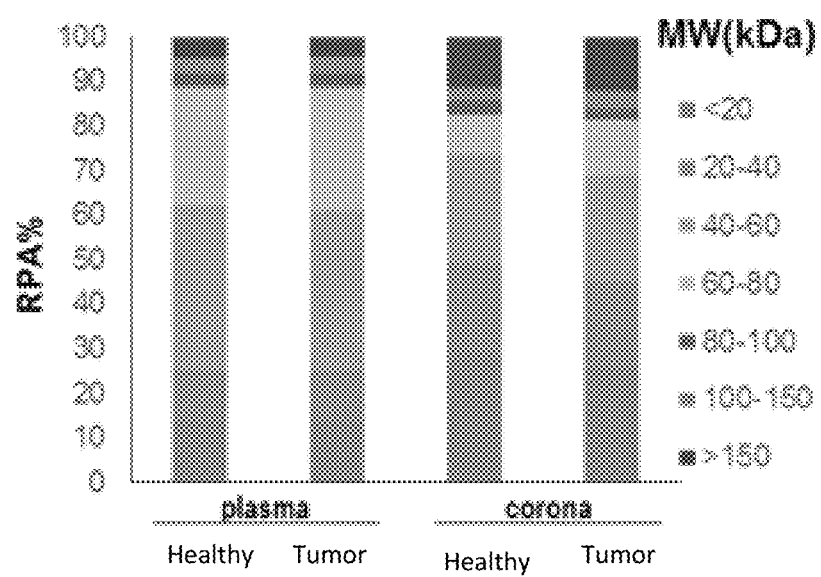
FIG. 14 is a melanoma model study showing surface-bound proteins that were also classified according to their molecular mass.

For the melanoma model study, surface-bound proteins were also classified according to their molecular mass as illustrated in FIG. 14. The RPA % values for each molecular weight group represents the average of 3 biological replicates (n=3 mice/replicate). As illustrated in FIG. 14, proteins with MW<60 kDa accounted for approximately 70% of the protein coronas formed, in both healthy and tumor-inoculated mice. Remarkably, analysis of the in vivo protein coronas increased the identification of proteins with MW<40 kDa, in comparison with plasma control analysis.

Figure 15:
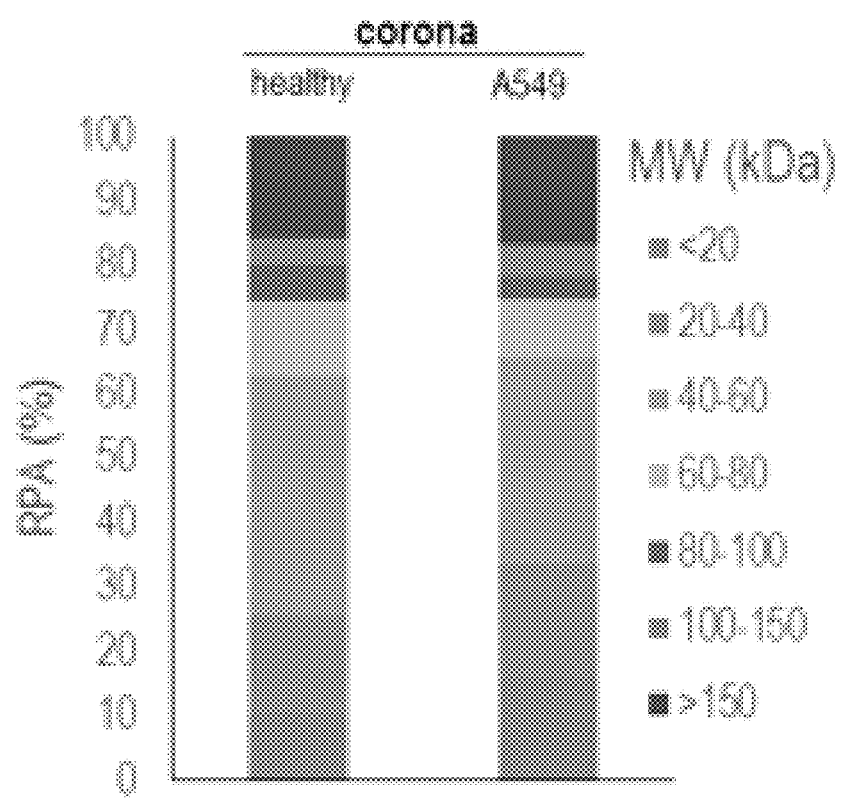
FIG. 15 is for a lung carcinoma study showing surface-bound proteins that were classified according to their molecular mass. A heatmap of RPA (%) of proteins identified in the coronas formed onto liposomes intravenously infused in healthy and lung-carcinoma mice, as identified by LC-MS/MS.

For the lung carcinoma study, surface-bound proteins were classified according to their molecular mass. A heatmap of RPA (%) of proteins identified in the coronas formed onto liposomes intravenously infused in healthy and lung-carcinoma mice, as identified by LC-MS/MS is shown in FIG. 15. Only proteins with RPA>0.5% are shown. RPA (%) values represent the average of 3 biological replicates (n=3 mice/replicate). Protein coronas formed in SCID mice were mainly composed of low MW proteins (>60% of corona proteins had a MW<60 kDa).

Quantification of Adsorbed Proteins

Proteins associated with recovered nanoparticles were quantified by BCA Protein assay kit. Pb values, expressed as µg of protein/µM lipid were then calculated. For the BCA assay, a 6-point standard curve was generated by serial dilutions of BSA in HBS, with the top standard at a concentration of 2 µg/ml. BCA reagent A and B were mixed at a ratio of 50:1 and 200 µl of the BCA mixture were dispensed into a 96-well plate, in duplicates. Then, 25 µl of each standard or unknown sample were added per well. The plate was incubated for 30 minutes at 37° C., after which the absorbance was read at 574 nm on a plate reader (Fluostar Omega). Protein concentrations were calculated according to the standard curve. To quantify lipid concentration, 20 µl of each sample was mixed with 1 ml of chloroform and 500 µl of Stewart assay reagent in an Eppendorf tube. The samples were vortexed for 20 seconds followed by 1 min of centrifugation at 13 000 RPM. 200 µl of the chloroform phase was transferred to a quartz cuvette. The optical density was measured on a using Cary 50 Bio Spectrophotometer (Agilent Technologies) at 485 nm. Lipid concentration was calculated according to a standard curve.

Statistical analysis of the data was performed using IBM SPSS Statistics software. One-way analysis of variance (ANOVA) followed by the Tukey multiple comparison test were used and p values<0.05 were considered significant.

Figure 6:
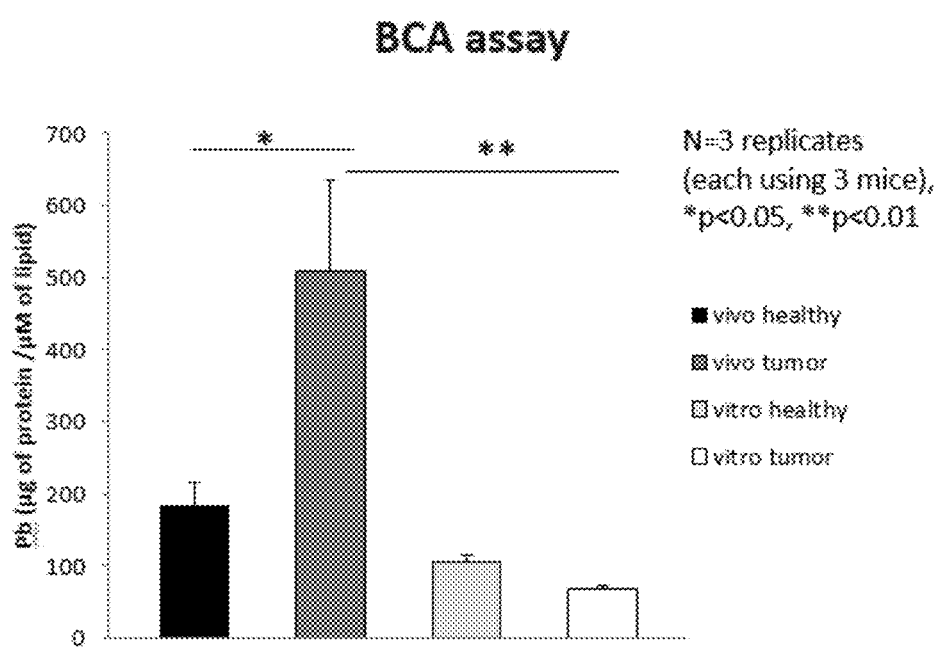
FIG. 6 provides data from a BCA assay for the lung adenocarcinoma model. The level of total amount of protein detected in the protein corona from tumor-bearing animals following in vivo administration is significantly greater than after in vitro incubation. Furthermore, there is a clear distinction between tumor and healthy mice in regards to the level of total amount of protein detected in the protein corona following in vivo administration.

FIG. 6 provides the results for the BCA assay for the lung adenocarcinoma model. Surprisingly, the level of total amount of protein detected in tumor-bearing animals following in vivo administration is significantly greater than after in vitro incubation. Furthermore, there is a clear distinction between tumor and healthy mice in regards to the level of total amount of protein detected in the protein corona following in vivo administration.

Figure 7:
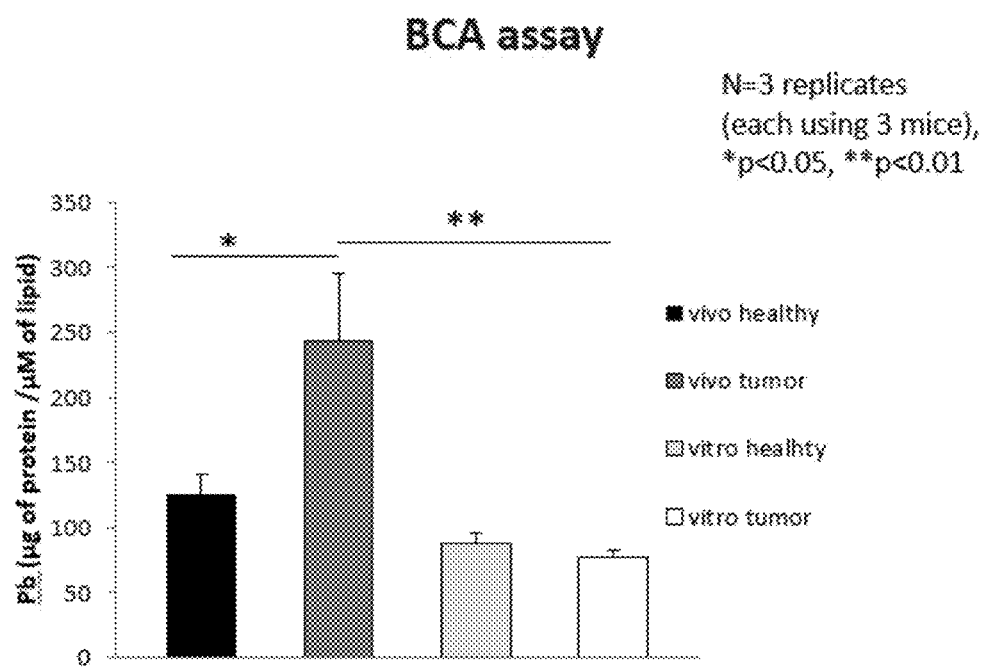
FIG. 7 provides data from a BCA assay for the melanoma model. The level of total amount of protein detected in the protein corona from tumor-bearing animals following in vivo administration is significantly greater than after in vitro incubation. Furthermore, there is a clear distinction between tumor and healthy mice in regards to the level of total amount of protein detected in the protein corona following in vivo administration.

A similar effect is observed for the for the melanoma model (FIG. 7).

Example 2 Human Experiments

Subjects

Eligible patients included women with recurrent ovarian cancer commencing liposomal doxorubicin (Caelyx) treatment for the first time.

Nanoparticles

Dynamic light scattering (DLS), ζ-potential measurements and negative stain transmission electron microscopy (TEM) data showing physicochemical characteristics of the PEGylated doxorubicin-encapsulated liposomes (Caelyx®) employed in this study before and after dosing are summarised in FIG. 12.

Dosing and Blood Sample Collection

Patients were intravenously infused with Caelyx (diluted in 5% dextrose) at a dose of 40 mg/m$^2$ for approximately 1.5 h. Collection of paired plasma samples (i.e. before and after cycle 1 infusion) were collected into commercially available anticoagulant-treated tubes (K2 EDTA BD Vacutainer). Plasma was then prepared by inverting the collection tubes 10 times to ensure mixing of blood with EDTA and subsequent centrifugation for 12 minutes at 1300 RCF at 4° C. Following centrifugation supernatant was immediately collected into labelled Protein LoBind Eppendorf Tubes and samples were maintained on ice while handling.

Protein Corona Formation after In Vitro Incubation of Nanoparticles with Plasma Taken from Patients Before Infusion The in vitro formed corona was allowed to form using a liposome concentration of 0.3 mM in plasma taken from patients before infusion, which is equivalent to the concentration of liposomes found in 1 ml of recovered plasma after in vivo administration to humans as described above. For all in vitro protein binding studies, 0.3 mM of liposomes (20 µl of 17 mM) were incubated with 980 µl of human patient plasma for 10 min at 37° C. in orbital shaker at 250 rpm setting to mimic in vivo conditions.

Separation of Corona-Coated Nanoparticles from Unbound and Weakly Bound Proteins Nanoparticles recovered from the in vivo human studies or the in vitro incubation method described above were separated from excess plasma proteins by size exclusion chromatography followed by membrane ultrafiltration Immediately after in vitro and in vivo incubations, 1 ml of plasma samples was loaded onto a Sepharose CL-4B (SIGMA-ALDRICH) column (15×1.5 cm) equilibrated with HBS. Stewart assay in each chromatographic fraction (1 ml) revealed that nanoparticles were eluted in fractions 4, 5 and 6. Fractions containing nanoparticles were then pooled together and concentrated to 500 µl by centrifugation using Vivaspin 6 column (10000 MWCO, Sartorious, Fisher Scientific) at 9000 rpm. Vivaspin 500 centrifugal concentrator (1 000 000 MWCO, Sartorious, Fisher Scientific) was then used at 9000 rpm, to further concentrate the samples to 100 µl and to ensure separation of protein-coated nanoparticles from the remaining large unbound proteins. Nanoparticles were then washed 3 times with 100 µl HBS to remove weekly bound proteins.

SDS-PAGE Electrophoresis

Samples of protein corona-coated nanoparticles were mixed with 20 µl of Tris-Glycine SDS buffer, with 4 ul of NuPAGE REDUCING and with water for a final volume of 40 µl and boiled for 5 minutes at 90° C. Samples were then loaded in 4-20% NOVEX Tris-Glycine Protein Gel (ThermoFisher Scientific). The gel was run for 25-40 minutes at 225V, until the proteins neared the end of the gel, in 10 times diluted Novex® Tris-Glycine SDS Running Buffer (ThermoFisher Scientific). Staining was performed with Imperial Gel Staining reagent (Sigma Life Science) for an hour followed by washing in distilled water for 2 days.

Figure 8:
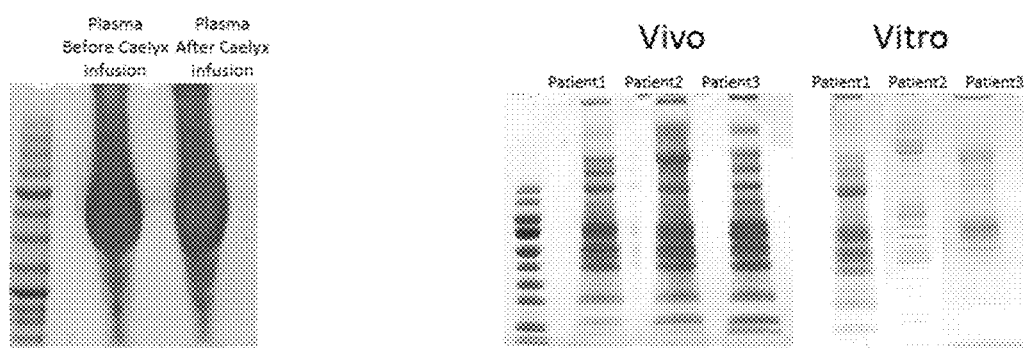
FIG. 8 shows the SDS-Page gel for protein recovered directly from plasma before and after infusion with Caelx and compares this with analysis conducted following either in vivo administration of nanoparticles or after in vitro incubation of nanoparticles with plasma taken from the human patients and shows that the masking problem with protein recovered directly from plasma is not present.

FIG. 8 shows the SDS-Page gel for protein recovered directly from plasma before and after infusion with Caelx. A large signal is present as a result of highly abundant proteins such as albumin. In contrast, the SDS-Page gel for analysis conducted following either in vivo administration of nanoparticles or after in vitro incubation of nanoparticles with plasma taken from the human patients shows that the masking problem is not present. The data shows the presence of a number of lower abundant proteins that would not be detectable by analyzing the plasma directly. Evidently, the amount of this lower abundant protein that would not be detectable by analyzing the plasma directly is higher for the samples analysed after in vivo administration of nanoparticles than the samples analysed after in vitro incubation with plasma taken from the human patients. This benefit may further aid detection of potential unique biomolecules by reducing the need for particular highly specialized and ultra-sensitive analytical mass spectrometry instrumentation.

Mass Spectrometry

Bands of interest were excised from the SDS-Page gel and dehydrated using acetonitrile followed by vacuum centrifugation. Dried gel pieces were reduced with 10 mM dithiothreitol and alkylated with 55 mM iodoacetamide. Gel pieces were then washed alternately with 25 mM ammonium bicarbonate followed by acetonitrile. This was repeated, and the gel pieces dried by vacuum centrifugation. Samples were digested with trypsin overnight at 37° C. Digested samples were analysed by LC-MS/MS using an UltiMate® 3000 Rapid Separation LC (RSLC, Dionex Corporation, Sunnyvale, Calif.) coupled to a Q Exactive™ Hybrid Quadrupole-Orbitrap™ (Thermo Fisher Scientific, Waltham, Mass.) mass spectrometer. Peptide mixtures were separated using a gradient from 92% A (0.1% FA in water) and 8% B (0.1% FA in acetonitrile) to 33% B, in 44 mM at 300 nL min$^{-1}$, using a 250 mm×75 µm i.d. 1.7 µM BEH C18, analytical column (Waters). Peptides were selected for fragmentation automatically by data dependent analysis. Data produced were searched using Mascot (Matrix Science UK), against the SwissProt_2016_04 databasedatabase. Data were validated using Scaffold (Proteome Software, Portland, Oreg.).

The Scaffold software (version Scaffold_4.4.5, Proteome Software Inc., Portland, Oreg.) was used to validate MS/MS based peptide and protein identifications and for relative quantification based on spectral counting. Peptide identifications were accepted if they could be established at greater than 50.0% probability by the Peptide Prophet algorithm with Scaffold delta-mass correction. Protein identifications were accepted if they could be established at greater than 99.0% probability and contained at least 2 identified peptides. Protein probabilities were assigned by the Protein Prophet algorithm. Proteins that contained similar peptides and could not be differentiated based on MS/MS analysis alone were grouped to satisfy the principles of parsimony. Semi quantitative assessment of the protein amounts was conducted using normalized spectral countings, NSCs, provided by Scaffold Software. The mean value of NSCs obtained in the three experimental replicates for each protein was normalized to the protein MW and expressed as a relative quantity by applying the following equation:

$$MWNSC_k = \frac{(NSC/MW)_k}{\sum_{i=1}^{N}(NSC/MW)_i} \times 100 \qquad (1)$$

where, MWNSCk is the percentage molecular weight normalized NSC for protein k and MW is the molecular weight in kDa for protein k. This equation takes into consideration the protein size and evaluates the contribution of each protein reflecting its relative protein abundance (RPA).

FIG. 9 provides a breakdown of the top 10 proteins identified with respect to percentage abundance following in vivo administration to 6 patients. The data demonstrates that the methods are able to extract out different types of proteins from the patients that are not readily detectable in plasma but are connected with cancer. FIG. 10 provides an extended list of proteins identified.

The accession numbers of the proteins indicated in FIGS. 9 and 10 were assigned using SwissProt_2016_04 database.

Figure 13:
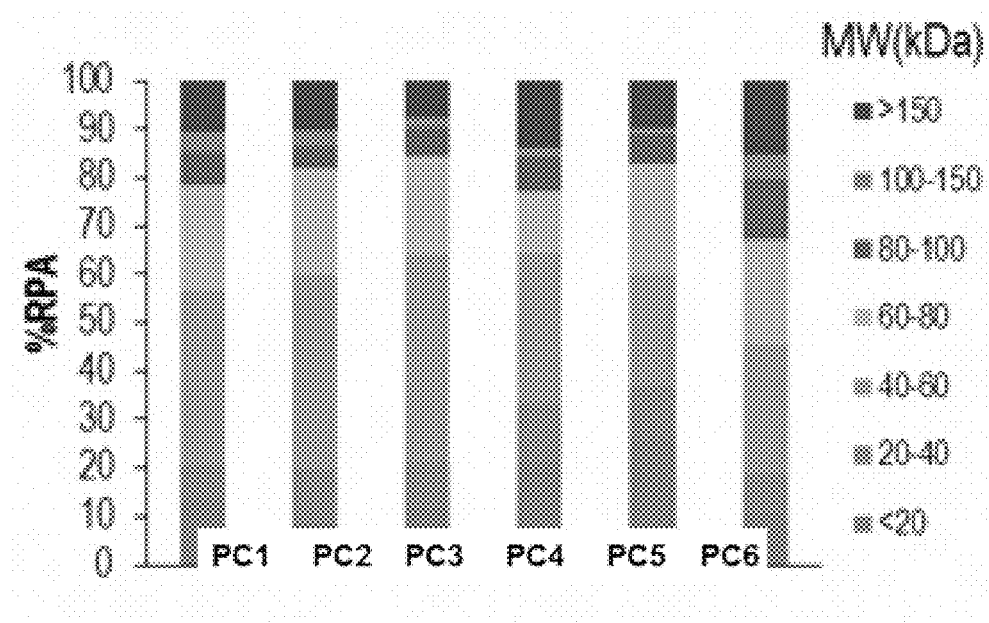
FIG. 13 shows surface-bound proteins that were also classified according to their molecular mass.

Surface-bound proteins were also classified according to their molecular mass as illustrated in FIG. 13. The percentage of relative protein abundance (% RPA) for each molecular weight group represent the average from 6 ovarian carcinoma patients. Plasma proteins with MW<80 kDA accounted for almost 80% of the protein coronas formed. It is possible that the low MW proteins identified (FIG. 13) have high affinity and interact directly with the surface of PEGylated liposomes and/or they are trapped between other corona-carrier proteins that are adhered to the nanoparticles surface.

Quantification of Adsorbed Proteins

Proteins associated with recovered nanoparticles were quantified by BCA Protein assay kit. Pb values, expressed as µg of protein/µM lipid were then calculated. For the BCA assay, a 6-point standard curve was generated by serial dilutions of BSA in HBS, with the top standard at a concentration of 2 µg/ml. BCA reagent A and B were mixed at a ratio of 50:1 and 200 µl of the BCA mixture were dispensed into a 96-well plate, in duplicates. Then, 25 µl of each standard or unknown sample were added per well. The plate was incubated for 30 minutes at 37° C., after which the absorbance was read at 574 nm on a plate reader (Fluostar Omega). Protein concentrations were calculated according to the standard curve. To quantify lipid concentration, 20 µl of each sample was mixed with 1 ml of chloroform and 500 µl of Stewart assay reagent in an Eppendorf tube. The samples were vortexed for 20 seconds followed by 1 min of centrifugation at 13 000 RPM. 200 µl of the chloroform phase was transferred to a quartz cuvette. The optical density was measured on a using Cary 50 Bio Spectrophotometer (Agilent Technologies) at 485 nm. Lipid concentration was calculated according to a standard curve.

Statistical analysis of the data was performed using IBM SPSS Statistics software. One-way analysis of variance (ANOVA) followed by the Tukey multiple comparison test were used and p values<0.05 were considered significant.

FIG. 11 provides the results for the BCA assay for the human patient study. The level of total amount of protein detected in the patients following in vivo administration is significantly greater than after in vitro incubation of the nanoparticles in plasma taken from such patients.

The invention claimed is:

1. A method of discovering unique disease-specific biomarker not previously known to be associated with the disease, wherein the method comprises:
   a. incubating a plurality of nanoparticles in a biofluid sample taken from a subject suffering from the disease and allowing a biomolecule corona to form on the surface of the nanoparticles;
   b. isolating the nanoparticles and surface-bound biomolecule corona;
   c. analyzing the isolated nanoparticles and surface-bound biomolecule corona by mass spectrometry and generating a mass spectrum;
   d. comparing the mass spectrum with a mass spectrum generated from a biofluid sample from a subject not suffering from the disease, which serves as a suitable non-diseased control reference, and identifying differences; and
   e. discovering a unique disease-specific biomarker not previously known to be associated with the disease based on the differences.

2. A method according to claim 1, wherein the nanoparticles are selected from liposomes, metallic nanoparticles, polymeric nanoparticles, fibre-shaped nanoparticles, and two dimensional nanoparticles.

3. A method according to claim 1, wherein the nanoparticles are liposomes.

4. A method according to claim 1, wherein the nanoparticles with surface-bound biomolecule corona are isolated from the biofluid and purified to remove unbound and highly abundant biomolecules to allow identification of low abundant biomarkers.

5. A method according to claim 4, wherein the nanoparticles with surface-bound biomolecule corona are isolated from the biofluid and purified to remove unbound and highly abundant biomolecules by a method comprising size exclusion chromatography followed by ultrafiltration.

6. A method according to claim 1, wherein a change in a biomarker in response to therapy is monitored.

7. A method according to claim 6, wherein the therapy administered to the subject prior to testing is a drug molecule.

8. A method according to claim 7, wherein the drug molecule is an anti-cancer compound.

9. A method according to claim 1, wherein the biomarker is a multiplex panel of disease-specific biomolecule biomarkers.

10. A method according to claim 1, wherein the biomarker is a unique biomolecule, meaning that it is a biomolecule that would not have been detected if analysis was carried out directly on biofluid, such as plasma, isolated from the subject.

11. A method according to claim 1, wherein the said disease is cancer.

12. A method according to claim 11, wherein the disease is lung cancer, melanoma or ovarian cancer.

13. A method according to claim 1, wherein the amount of the unique disease-specific biomarker not previously known to be associated with the disease is 5-fold more or greater than the amount in the non-diseased control reference.

* * * * *